(12) United States Patent
Howard et al.

(10) Patent No.: US 11,207,131 B2
(45) Date of Patent: Dec. 28, 2021

(54) REVERSE IRRIGATION FOR EMBOLIC MITIGATION

(71) Applicant: Medtronic, Inc., Minneapolis, MN (US)

(72) Inventors: Brian T. Howard, Hugo, MN (US); Steven V. Ramberg, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 779 days.

(21) Appl. No.: 15/651,828

(22) Filed: Jul. 17, 2017

(65) Prior Publication Data

US 2019/0015152 A1  Jan. 17, 2019

(51) Int. Cl.
*A61B 18/14* (2006.01)
*A61B 18/00* (2006.01)
(Continued)

(52) U.S. Cl.
CPC .......... *A61B 18/1492* (2013.01); *A61B 5/352* (2021.01); *A61B 2018/00029* (2013.01);
(Continued)

(58) Field of Classification Search
CPC ...... A61B 18/1492; A61B 2018/00029; A61B 2018/00577; A61B 2018/00613; A61B 2018/00642; A61B 2018/00839; A61B 2018/00988; A61B 2018/0212; A61B 2018/1407; A61B 2018/1435; A61B 2018/1467; A61B 2218/007; A61B 5/0456

See application file for complete search history.

(56) References Cited

U.S. PATENT DOCUMENTS 3,974,833 A * 8/1976 Durden, III ........ A61B 18/1402
604/20
5,197,949 A * 3/1993 Angsupanich .............................
A61B 17/320708
600/571

(Continued)

OTHER PUBLICATIONS

International Search Report and Written Opinion dated Jun. 29, 2018 for corresponding International Application No. PCT/US2018/027096; International Filing Date: Apr. 11, 2018 consisting of 12-pages.

*Primary Examiner* — Michael F Peffley
*Assistant Examiner* — Amanda L Zink
(74) *Attorney, Agent, or Firm* — Christopher & Weisberg, P.A.

(57) ABSTRACT

Devices, systems, and methods for reverse irrigation of an ablation or treatment site. In one embodiment, a reverse irrigation device comprises at least one ablation electrode and at least one reverse irrigation port, the at least one reverse irrigation port being located at at least one of immediately proximate the at least one ablation electrode and on the at least one ablation electrode, the at least one reverse irrigation port being configured to be in fluid communication with a fluid removal component. A medical system may include an ablation system and a reverse irrigation system that are configured to operate synchronously such that the reverse irrigation system is activated to remove fluid from the ablation site during a period of time during which the ablation system is activated to deliver ablation energy through the at least one ablation electrode to the ablation site.

11 Claims, 14 Drawing Sheets

(51) Int. Cl.
  *A61B 18/02*  (2006.01)
  *A61B 5/352*  (2021.01)
(52) U.S. Cl.
  CPC ............... *A61B 2018/00577* (2013.01); *A61B 2018/00613* (2013.01); *A61B 2018/00642* (2013.01); *A61B 2018/00839* (2013.01); *A61B 2018/00988* (2013.01); *A61B 2018/0212* (2013.01); *A61B 2018/1407* (2013.01); *A61B 2018/1435* (2013.01); *A61B 2018/1467* (2013.01); *A61B 2218/007* (2013.01)

(56) References Cited

U.S. PATENT DOCUMENTS

| | | | | |
|---|---|---|---|---|
| 5,295,956 A * | 3/1994 | Bales | .................. | A61M 1/0045 |
| | | | | 604/119 |
| 5,609,573 A * | 3/1997 | Sandock | ............ | A61B 18/1482 |
| | | | | 604/22 |
| 5,885,238 A | 3/1999 | Stevens et al. | | |
| 6,254,600 B1 * | 7/2001 | Willink | ................ | A61B 18/149 |
| | | | | 606/41 |
| 6,605,074 B2 | 8/2003 | Zadno-Azizi et al. | | |
| 7,150,713 B2 * | 12/2006 | Shener | ............... | A61B 1/00071 |
| | | | | 600/156 |
| 7,625,207 B2 * | 12/2009 | Hershey | ................... | A61C 1/16 |
| | | | | 433/91 |
| 7,678,069 B1 | 3/2010 | Baker et al. | | |
| 9,993,585 B2 * | 6/2018 | Riordan | ................ | A61M 1/008 |
| 2005/0096647 A1 * | 5/2005 | Steinke | ............... | A61B 18/1492 |
| | | | | 606/41 |
| 2008/0009747 A1 * | 1/2008 | Saadat | ..................... | A61B 1/04 |
| | | | | 600/471 |
| 2009/0125017 A1 | 5/2009 | Wang et al. | | |
| 2011/0028939 A1 * | 2/2011 | Yarger | .................. | A61M 1/008 |
| | | | | 604/523 |
| 2011/0230799 A1 | 9/2011 | Christian et al. | | |
| 2011/0306970 A1 * | 12/2011 | Razavi | ............. | A61M 25/0662 |
| | | | | 606/41 |
| 2014/0058386 A1 * | 2/2014 | Clark | ..................... | A61B 18/14 |
| | | | | 606/41 |
| 2014/0142569 A1 * | 5/2014 | Plascencia, Jr. | ...... | A61B 18/082 |
| | | | | 606/41 |
| 2014/0276743 A1 * | 9/2014 | Curley | ............... | A61B 18/1815 |
| | | | | 606/33 |
| 2015/0066005 A1 * | 3/2015 | Fan | .................... | A61B 18/0218 |
| | | | | 606/21 |
| 2016/0120592 A1 | 5/2016 | Sylvester et al. | | |
| 2016/0278844 A1 | 9/2016 | Zamarripa et al. | | |
| 2016/0374755 A1 | 12/2016 | Mirigian et al. | | |

\* cited by examiner (1)

REVERSE IRRIGATION FOR EMBOLIC MITIGATION

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to devices, systems, and methods for reverse irrigation of an ablation or treatment site.

BACKGROUND

Tissue ablation is a medical procedure that is often performed for the treatment of certain cardiac conditions, such as arrhythmias caused by aberrant electrical conduction through the myocardial tissue. Various energy modalities may be used for tissue ablation, including cryoablation, radiofrequency ablation, laser ablation, and electroporation, to name a few. The success of the procedure largely depends on the location and depth of the tissue lesion produced from the ablation procedure. That is, if the lesion does not extend deeply enough within the target tissue (e.g., if the lesion is not transmural), the aberrant electrical conduction may not be affected or may return after the procedure has been performed. When using certain energy modalities such as radiofrequency ablation, high voltages and relatively long ablation times may be required to produce lesions with sufficient depth.

However, high energy levels and extended ablation times also increases the risk of the occurrence of thromboembolic events. When radiofrequency energy is delivered to tissue, that energy is converted to heat within the tissue near the ablation electrodes and the heat is then transferred to surrounding tissue through radiation and conduction. Although this effect contributes to lesion formation, thermal energy is also delivered to the surrounding blood. Heating the surrounding blood can lead to the formation of bubbles, coagulum, and/or char, which has the potential to travel through the patient's vasculature and cause thromboembolic events. Further, tissue may easily become overheated by the ablation procedure, which can lead to tissue rupture, the formation of microbubbles at the ablation site, and the formation of thromboembolic debris.

To prevent microbubble formation and the associated occurrence of undesired effects such as blood boiling and vaporization, clot formation and formation of other thromboembolic debris, impedance increase at the ablation site, movement of the ablation device, and tissue cleavage, some ablation devices are irrigated, meaning they are configured to deliver a biocompatible fluid such as saline to the ablation site. This delivery of irrigation fluid may not only reduce the temperature of the ablation electrodes and the tissue being ablated, but may also decrease the occurrence or likelihood of the formation of microbubbles and thromboembolic debris. However, during long during long application times, the amount of fluid introduced to a patient through irrigation can be significant. Accordingly, more efficient removal of fluid and debris from the ablation site is desired.

SUMMARY

The present invention advantageously provides devices, systems, and methods for reverse irrigation of an ablation or treatment site. For example, a reverse irrigation device may be used to remove fluid form an ablation site during a period of time over which ablation energy is delivered to the ablation site. In one embodiment, a reverse irrigation device comprises at least one ablation electrode and at least one reverse irrigation port, the at least one reverse irrigation port being located at at least one of immediately proximate the at least one ablation electrode and on the at least one ablation electrode, the at least one reverse irrigation port being configured to be in fluid communication with a fluid removal component.

In one aspect of the embodiment, the at least one reverse irrigation port is on the at least one ablation electrode.

In one aspect of the embodiment, the at least one reverse irrigation port has an at least substantially circular shape.

In one aspect of the embodiment, the at least one reverse irrigation port has an elongate shape.

In one aspect of the embodiment, the reverse irrigation medical device further comprises an elongate body having a distal portion, a proximal portion opposite the distal portion, and a longitudinal axis, the at least one ablation element including a plurality of ablation electrodes on the elongate body distal portion and the at least one reverse irrigation port including a plurality of reverse irrigation ports.

In one aspect of the embodiment, the plurality of ablation electrodes includes a first ablation electrode and a second ablation electrode located distal to the first ablation electrode; and the first ablation electrode includes a first plurality of reverse irrigation ports and the second ablation electrode includes a second plurality of reverse irrigation ports.

In one aspect of the embodiment, each of the first plurality of reverse irrigation ports has a first diameter and each of the second plurality of reverse irrigation ports has a second diameter that is greater than the first diameter.

In one aspect of the embodiment, the first plurality of reverse irrigation ports includes a first number of reverse irrigation ports and the second plurality of reverse irrigation ports includes a second number of reverse irrigation ports that is greater than the first number of reverse irrigation ports.

In one aspect of the embodiment, at least one of the first plurality of reverse irrigation ports has a first diameter and at least one of the second plurality of reverse irrigation ports has a second diameter that is greater than the first diameter.

In one aspect of the embodiment, the first plurality of reverse irrigation ports includes a first number of reverse irrigation ports and the second plurality of reverse irrigation ports includes a second number of reverse irrigation ports that is greater than the first number of reverse irrigation ports.

In one aspect of the embodiment, the at least one reverse irrigation port is immediately adjacent the at least one ablation electrode.

In one aspect of the embodiment, the reverse irrigation device further comprises: an elongate body having a distal portion, a proximal portion opposite the distal portion, and a longitudinal axis; the at least one ablation element including a plurality of elongate ablation electrodes on the elongate body distal portion, the plurality of elongate ablation electrodes being radially offset from and parallel to the elongate body longitudinal axis; and the at least one reverse irrigation port including a plurality of elongate reverse irrigation ports being alternated with the plurality of elongate ablation electrodes, the plurality of elongate reverse irrigation ports being radially offset from and parallel to the elongate body longitudinal axis.

In one aspect of the embodiment, each of the elongate reverse irrigation ports has a proximal end and a distal end, each of the elongate reverse irrigation ports being tapered such that the reverse irrigation port proximal end has a first diameter and the reverse irrigation port distal end has a second diameter that is greater than the first diameter of the reverse irrigation port proximal end; and each of the elongate ablation electrodes has a proximal end and a distal end, each of the elongate ablation electrodes being tapered such that the ablation electrode proximal end has a first diameter and the ablation electrode distal end has a second diameter that is less than the first diameter of the ablation electrode proximal end.

In one aspect of the embodiment, the reverse irrigation device further comprises: an elongate body having a distal portion, a proximal portion opposite the distal portion, a longitudinal axis, and a circumference, the at least one ablation electrode including a plurality of arcuate electrodes, each of the plurality of arcuate electrodes being on the elongate body distal portion and extending around less than an entirety of the circumference of the elongate body such that each of the plurality of arcuate electrodes defines a gap; and a reverse irrigation band on the elongate body distal portion, the reverse irrigation band being at least substantially parallel to the elongate body longitudinal axis and extending within the gap defined by each of the plurality of arcuate electrodes, the at least one reverse irrigation port including a plurality of reverse irrigation ports that are on the reverse irrigation band.

In one aspect of the embodiment, the reverse irrigation device further comprises an elongate body having a distal portion including a distal end, and a proximal portion opposite the distal portion, the at least one ablation electrode including a distal tip electrode coupled to the distal end of the elongate body, the distal tip electrode including a plurality of elongate portions, and the at least one reverse irrigation port including a plurality of elongate reverse irrigation ports alternating with the plurality of elongate portions of the distal tip electrode.

In one aspect of the embodiment, each of the plurality of reverse irrigation ports includes: a first portion defining an opening in the distal end of the elongate body; and a second portion that is configured to channel fluid over the distal tip electrode and into the opening of the first portion of the at least one reverse irrigation port.

In one aspect of the embodiment, the fluid removal component is a vacuum pump.

In one embodiment, a reverse irrigation sheath for use with a medical device comprises: at least one lumen configured to be in fluid communication with a vacuum pump; and at least one reverse irrigation port in fluid communication with the at least one lumen.

In one aspect of the embodiment, the at least one lumen is a central lumen, the reverse irrigation sheath further comprising: a wall, the wall at least partially defining the central lumen, the at least one reverse irrigation port extending through the wall to the central lumen.

In one aspect of the embodiment, the at least one reverse irrigation port includes a plurality of reverse irrigation ports, each of the plurality of reverse irrigation ports having one of a linear shape and a circular shape.

In one aspect of the embodiment, the at least one reverse irrigation port includes a mesh.

In one aspect of the embodiment, the reverse irrigation sheath further comprises: a distal end defining a distal opening, the distal opening being in fluid communication with the at least one lumen.

In one aspect of the embodiment, the distal opening has a scalloped shape.

In one embodiment, a medical system comprises: a medical device, the medical device including at least one ablation electrode and at least one reverse irrigation port; an ablation system in communication with the medical device; and a reverse irrigation system, the reverse irrigation system including a vacuum pump, the vacuum pump being in fluid communication with the at least one reverse irrigation port such that the at least one reverse irrigation port is configured to remove fluid from an ablation site during an ablation procedure.

In one aspect of the embodiment, the ablation system includes processing circuitry and an energy generator in communication with the at least one ablation electrode; and the reverse irrigation system includes processing circuitry in communication with the vacuum pump and the ablation system processing circuitry, the ablation system processing circuitry and the reverse irrigation processing circuitry being configured to operate synchronously such that the vacuum pump is activated to remove fluid from the ablation site during a period of time during which the energy generator is activated to deliver ablation energy through the at least one ablation electrode to the ablation site.

In one embodiment, a medical system comprises: a medical device, the medical device including at least one ablation electrode and at least one reverse irrigation port; an ablation system in communication with the medical device; and a reverse irrigation system, the reverse irrigation system being in communication with the ablation system and being configured to: initiate a withdrawal of fluid from a treatment site through the at least one reverse irrigation port, the initiation being at a predetermined period of time before a delivery of ablation energy by the ablation system; and terminate the withdrawal of fluid a treatment site through the at least one reverse irrigation port, the termination being at a predetermined period of time after the delivery of ablation energy by the ablation system.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
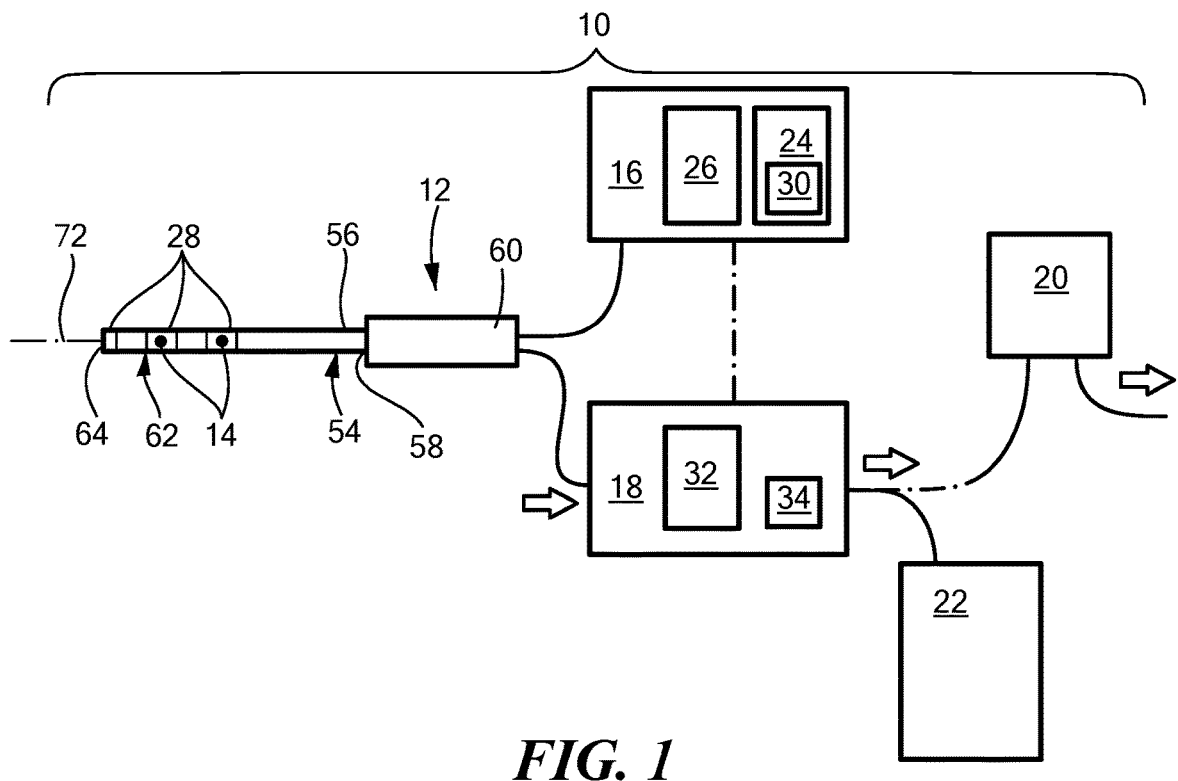
FIG. 1 shows a schematic image of an exemplary medical system having a reverse irrigation medical device.

The devices, systems, and methods described herein relate to reverse irrigation, or the removal of fluid from an ablation site, during an ablation procedure. The removal of fluid from the ablation site may reduce the likelihood of serious adverse events such as aneurism or cardiac infarction occurring as a result of ablation. Before describing in detail exemplary embodiments, it is noted the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to FIG. 1, an exemplary medical system having a reverse irrigation device is shown. The medical system 10 may generally include a medical device 12 having one or more reverse irrigation ports 14, an ablation system 16 in communication with the medical device 12, and a reverse irrigation system 18 in fluid communication with the medical device 12 and in communication with the ablation system 16. Optionally, the medical system 10 may further include a fluid reclamation system 20 and/or a waste removal system 22.

The ablation system 16 may include one or more system components for the delivery, control, and monitoring of ablation energy. The ablation system 16 may be configured for use with one or more ablation energy modalities, such as radiofrequency ablation, electroporation, laser ablation, microwave ablation, or the like. The ablation system 16 may include a control unit 24 having an energy generator 26. In one embodiment, the control unit 24 may include an energy generator 26 for the delivery of irreversible and/or reversible electroporation energy. The ablation system 16 may be in communication with the medical device 12 such that energy is delivered from the ablation system 16 through one or more electrodes 28 or other ablation or treatment elements on the medical device 12, as is described in more detail below. The control unit 24 may further include one or more controllers, processors, and/or software modules containing instructions or algorithms to provide for the automated operation and performance of the features, sequences, or procedures described herein. For example, the control unit 24 unit may include processing circuitry 30 with a memory and a processor. The memory may be in electrical communication with the processor and may have instructions that, when executed by the processor, configure the processor to receive, process, or otherwise use signals from the medical device 12 and/or other system components. Further, the control unit 24 may include one or more user input devices, controllers, and/or displays for collecting and conveying information from and to the user.

Although not shown, the medical system 10 may include one or more sensors to monitor the operating parameters through the medical system 10, such as pressure, temperature, delivered voltage, or the like, and for measuring and monitoring one or more tissue characteristics, such as ECG waveforms, tissue impedance, or the like, in addition to monitoring, recording, or otherwise conveying measurements or conditions within the device or other component of the medical system 10 or the ambient environment at the distal portion of the medical device 12. The sensor(s) may be in communication with the control unit 24 for initiating or triggering one or more alerts or ablation energy delivery modifications during operation of the medical device 12.

The reverse irrigation system 18 may include one or more components for the removal of fluid, thromboembolic debris, bubbles/microbubbles (collectively referred to herein as bubbles), and/or other product of ablation from an ablation site. In one embodiment, the reverse irrigation system 18 may include a fluid removal component, such as a vacuum pump, syringe pump, or vacuum containers 32 that exert suction on the reverse irrigation ports 14 or a system component that is configured to remove fluid by gravity, non-active vacuum, and/or the like through the reverse irrigation ports 14. The reverse irrigation system 18 may include one or more controllers, processors, and/or software modules containing instructions or algorithms to provide for the automated operation and performance of the features, sequences, or procedures described herein. For example, the control unit may include processing circuitry 34 with a memory and a processor. The memory may be in electrical communication with the processor and may have instructions that, when executed by the processor, configure the processor to receive, process, or otherwise use signals from the device. The processing circuitry 34 of the reverse irrigation system 18 may be in wired or wireless communication with the processing circuitry 30 of the ablation system 16.

Reverse irrigation during ablation may recover bubbles, gas, bodily fluid, blood, charred tissue, and/or other materials from the vicinity of the ablation site and/or produced as biological byproducts of the ablation procedure. These materials may be collectively referred to herein as fluid for simplicity. In currently known systems, this fluid is not collected and this can cause serious adverse events such as aneurism or cardiac infarction. Fluid recovered from an ablation site by the reverse irrigation system 18 may be collected as waste and disposed of accordingly, such as by a waste removal system 22. Alternatively, the fluid may pass into a fluid reclamation system 20 for treatment, processing, and/or reintroduction into the patient. For example, if a large enough volume of blood is collected through reverse irrigation, the fluid reclamation system 20 may be used to remove the embolic gas/material (such as with a cell saver system) so that the blood may be reintroduced into the patient's circulation. This blood may be reintroduced continuously, as a bolus, or periodically, and may be reintroduced through the medical device and/or through secondary access to the patient.

Figure 2:
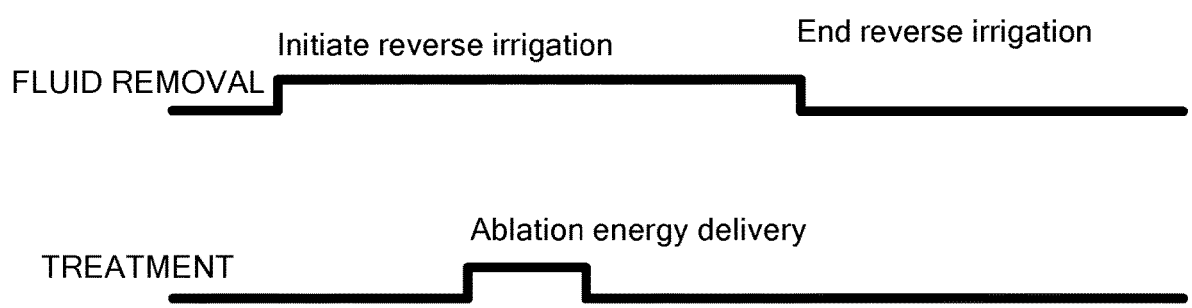
FIG. 2 shows an exemplary timing of a method of treating tissue with a reverse irrigation medical device.

The communication between the ablation system 16 and the reverse irrigation system 18 may be used to determine proper timing for both fluid recovery and ablation and/or to automatically synchronize fluid recovery and ablation. As shown in FIG. 2, fluid removal by the reverse irrigation system 18 may be synchronized with the delivery of ablation energy, such as electroporation energy, such that the reverse irrigation system 18 is activated prior to the ablation energy delivery and continues for a period of time after the cessation of ablation energy delivery to recover as much fluid as possible. In one embodiment, the processing circuitry 30 of the ablation system 16 and the processing circuitry 34 of the reverse irrigation system 18 may be configured to operate synchronously such that the reverse irrigation system 18 removes fluid from an ablation site (that is, the vacuum pump 32 or other fluid removal component is activated) during the entire period of energy delivery to the ablation site by the ablation system 16. An electroporation procedure may be executed in a much faster time frame and draw a relatively small volume of fluid over the course of delivery (for example, between less than 1.0 ml to approximately 50 ml). Fluid recovery may be initiated (for example, through activation of the fluid recovery system, such as by activation of the vacuum pump 32 or other fluid removal component) between approximately one and two seconds before the activation of the energy source used to deliver ablation energy. For example, electroporation energy may be delivered for a period of approximately 100 μs, and delivery may be timed to the refractory portion of the cardiac cycle, during the approximately 250 ms following the R-wave. In on embodiment, a pending electroporation energy delivery may be initiated and the actual delivery of the electroporation energy may be allowed following an R-wave detection after an appropriate period of time has elapsed since the pending electroporation energy delivery was initiated. Additionally, the automatic synchronization between the ablation system 16 and the reverse irrigation system 18 may allow the operator to activate both ablation and fluid recovery using a single activation input through either the ablation system 16 and/or the reverse irrigation system 18. However, it will be understood that the reverse irrigation system 18 may be continuously and manually or semi-automatically engaged during the procedure at an operator's discretion without these timing efforts, in which case the fluid reclamation system 20 may be operated to allow the return of usable blood and/or blood components to the patient to reduce loss over the course of the procedure.

Figure 3:
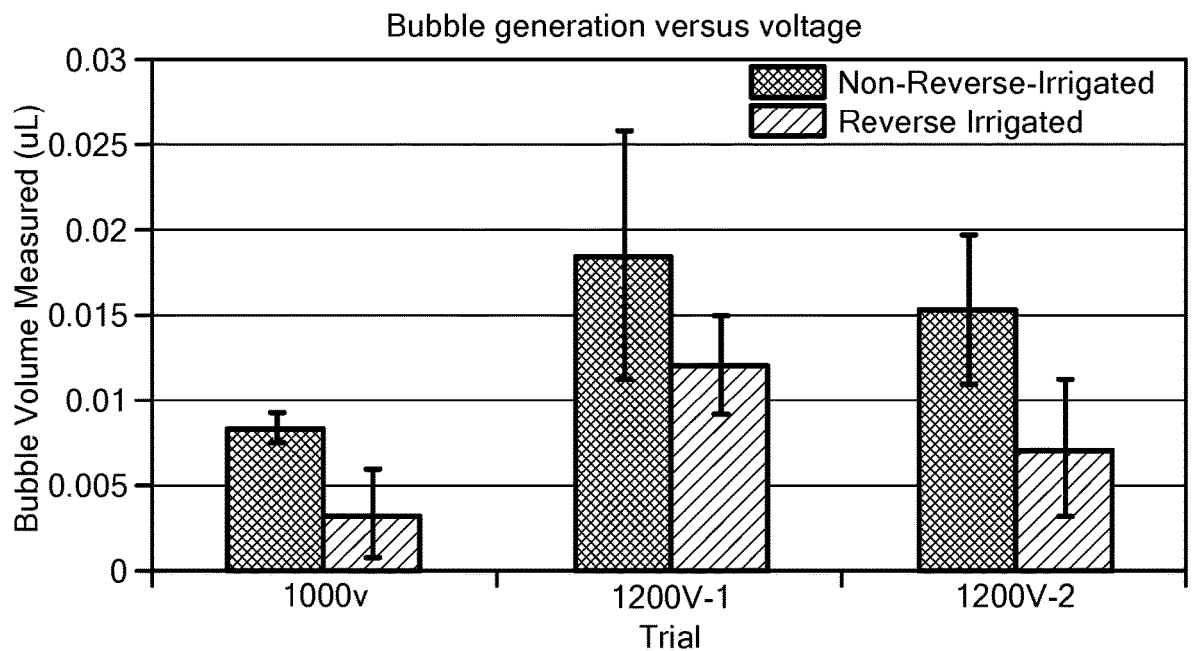
FIG. 3 shows an exemplary chart comparing fluid volume at an ablation site for reverse-irrigated energy delivery and non-reverse-irrigated energy delivery.

Referring now to FIG. 3, an exemplary chart comparing fluid volume at an ablation site for reverse-irrigated energy delivery and non-reverse-irrigated energy delivery is shown. Data used to generate this chart was obtained by electroporating tissue in vitro in a sealed environment, and the volume of bubbles generated by the electroporation and remaining in the ablation site within the sealed environment was quantified. When a reverse irrigation medical device 12 was used, many of the resulting bubbles were removed from the sealed environment as discussed herein, and therefore were not included in the total volume remaining at the ablation site. As is shown in FIG. 3, reverse irrigation during the delivery of electroporation energy at both 1000 V and at 1200 V resulted in a smaller volume of bubbles remaining at the ablation site than the delivery of electroporation energy without reverse irrigation. Thus, this data suggest that the risk of adverse effects caused by tissue ablation (such as aneurism or cardiac infarction) is reduced when using reverse irrigation during energy delivery. Additionally, this shows that the use of reverse irrigation may allow higher levels of ablation energy to be applied to the tissue without increasing the risk of adverse effects. For example, for electroporation, a much high voltage and/or pulse width, both of which may contribute to bubble and fluid formation, may be used to target deeper tissue such as in the ventricles of the heart or to penetrate scar tissue from previous ablations.

Figure 4:
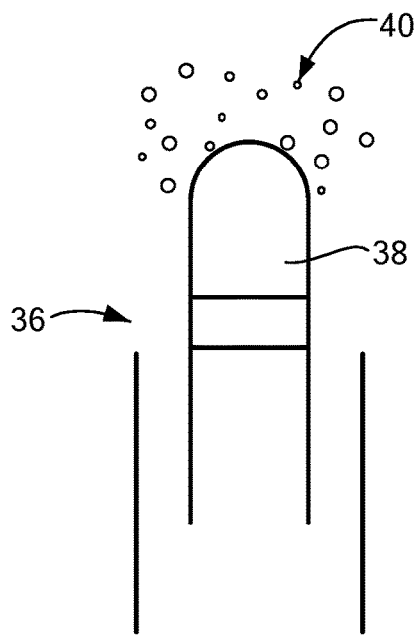
FIG. 4 shows a simplified image of a prior art medical device without reverse irrigation.

Referring now to FIG. 4, a simplified image of a prior art non-reverse-irrigation medical device 36 is shown. In general, the medical device 36 may include one or more ablation elements 38, such as, but not limited to, a distal tip electrode 38 as shown in FIG. 4. Ablation of tissue with the ablation element 38 may cause bubble formation, tissue charring, release of fluids from the tissue cells, coagulated blood, and/or the creation of other biological byproducts and potential emboli (collectively referred to herein as fluid 40). When using currently known medical devices without reverse irrigation, or when using currently known irrigated medical devices, the fluid 40 remains at the ablation site (and/or is transported through the patient's vasculature) and is not removed from the ablation site by the medical device 36. Thus, this fluid has the potential to generate embolic effects.

Figure 5:
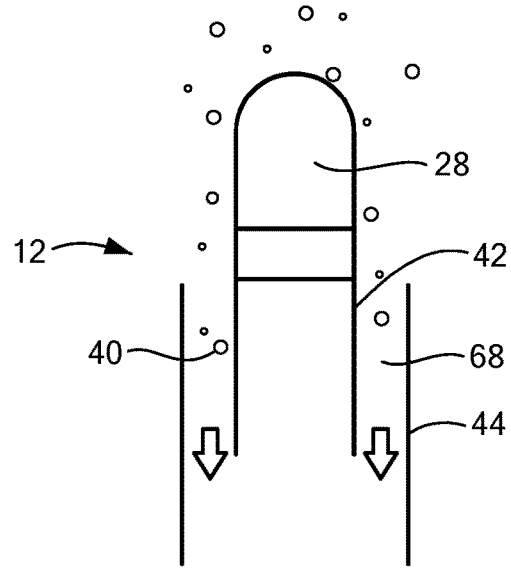
FIG. 5 shows a simplified image of a first embodiment of a reverse irrigation medical device.
Figure 7:
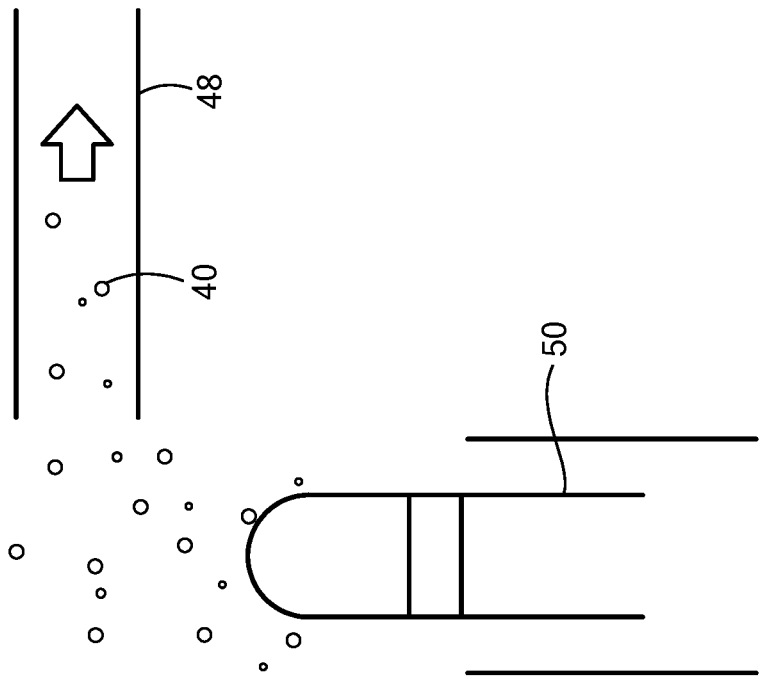
FIG. 7 shows a simplified image of a third embodiment of a reverse irrigation medical device, the reverse irrigation medical device being configured for use with a separate ablation device.
Figure 6:
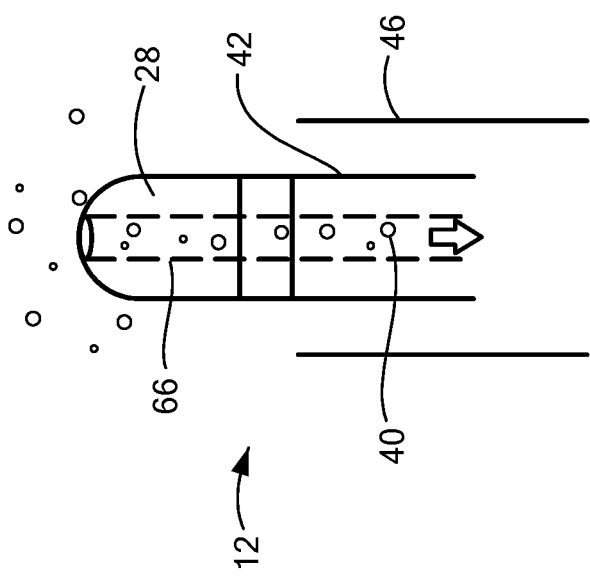
FIG. 6 shows a simplified image of a second embodiment of a reverse irrigation medical device.

Referring now to FIGS. 5-7, three embodiments of reverse irrigation medical devices 12 are shown. As shown in FIG. 5, the reverse irrigation medical device 12 may include an ablation device 42 and a reverse irrigation sheath 44, and the reverse irrigation sheath 44 may be in fluid communication with the reverse irrigation system 18 for removal of fluid 40 from the ablation site (as shown by arrows). Additionally or alternatively, as shown in FIG. 6, the reverse irrigation medical device 12 may also include one or more ablation elements, such as electrodes 28, and the reverse irrigation medical device 12 may be in fluid communication with the reverse irrigation system 18 for fluid removal from the ablation site (as shown by the arrow). In one embodiment, the reverse irrigation medical device 12 may be used alone or may optionally include a sheath 46 that is not in fluid communication with the reverse irrigation system 18. Additionally or alternatively, as shown in FIG. 7, the medical system 10 may include a reverse irrigation first device 48 and an ablation second device 50. The reverse irrigation first device 48 may be in fluid communication with the reverse irrigation system 18 for fluid removal from the ablation site (shown by the arrow), whereas the ablation second device 50 may be configured to ablate tissue but may not be in fluid communication with the reverse irrigation system 18. The various reverse irrigation device configurations discussed herein may generally fall into one of these three embodiments; however, it will be understood that a reverse irrigation medical device 12 may include more than one means for fluid removal. For example, a reverse irrigation medical device 12 may include one or more ablation elements, such as electrodes 28, and a reverse irrigation sheath 44, both the medical device 12 and sheath 46 being in fluid communication with the reverse irrigation system 18.

As is discussed in greater detail below, the reverse irrigation medical device 12 may include one or more reverse irrigation conduits 52 for transporting fluid from the ablation site to a waste removal system 22 and/or the fluid reclamation system 20. Thus, the reverse irrigation conduit(s) 52 may be in fluid communication with the reverse irrigation port(s) 14 of the medical device 12, the vacuum pump 32 or other fluid removal components of the reverse irrigation system 18, and the waste removal system 22 and/or the fluid reclamation system 20. The reverse irrigation medical device 12 may include an elongate body 54 having a proximal portion 56 with a proximal end 58 coupled to a handle 60, a distal portion 62 with a distal end 64, one or more lumens or conduits 66 for various device components (for example, pull wires, electrode wires, irrigation conduits, or the like). In embodiments wherein the medical device 12 includes reverse irrigation ports 14 on the medical device 12, the elongate body 54 may also include one or more reverse irrigation conduits 52 that extend through the elongate body 54, from the proximal portion 56 to the reverse irrigation port(s) 14 in the distal portion 62. In embodiments wherein the medical device 12 additionally or alternatively includes a reverse irrigation sheath 44 in fluid communication with the reverse irrigation system 18, the sheath 44 may include a lumen 68 that itself may provide the reverse irrigation conduit and/or the sheath 44 may include one or more reverse irrigation conduits 52 within the sheath wall and/or sheath lumen 68.

Figure 8:
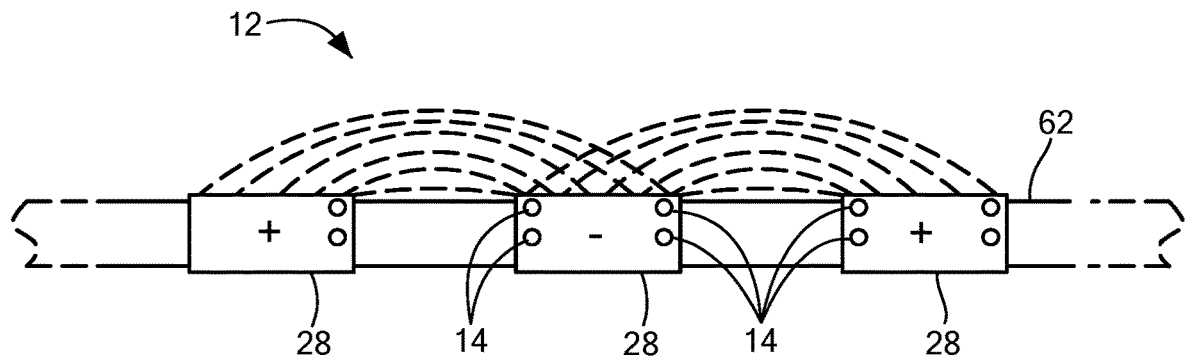
FIG. 8 shows an exemplary energy distribution pattern and placement of reverse irrigation ports.

Referring now to FIG. 8, an exemplary energy distribution pattern (shown as dashed lines) and placement of reverse irrigation ports 14 are shown. In one embodiment, a reverse irrigation medical device 12 (a portion of which is shown in the non-limiting example of FIG. 8) may include a plurality of ablation elements, such as electrodes 28, along a length of the distal portion 62 of the elongate body 54, which electrodes 28 may be configured to deliver energy in a bipolar mode and/or a monopolar mode. The electrodes 28 may have any suitable shape and/or configuration, such as band electrodes, elongate electrodes, spot electrodes, spiral electrodes, clusters of electrodes, discrete electrodes, or the like. The reverse irrigation ports 14 may be located proximate areas of higher current/voltage field density, which may be correlated to areas of increased bubble and fluid production. In one non-limiting example, when delivering energy in bipolar mode, such as electroporation energy, the energy fields may be at least somewhat concentrated at or proximate the edges of the electrodes 28. Therefore, it may be desirable to locate one or more reverse irrigation ports 14 proximate these areas, as a greater amount of fluid 40 may be generated from tissue in contact with the device at these areas. Although the reverse irrigation ports 14 are shown as being circular, or at least substantially circular, in FIG. 8, it will be understood that the reverse irrigation ports 14 may have any suitable size, shape, or configuration.

Figure 9:
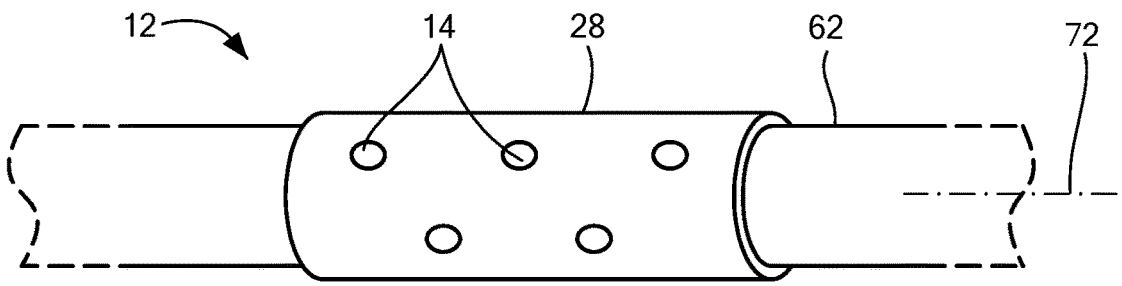
FIG. 9 shows a first embodiment of a band electrode having reverse irrigation ports.
Figure 10:
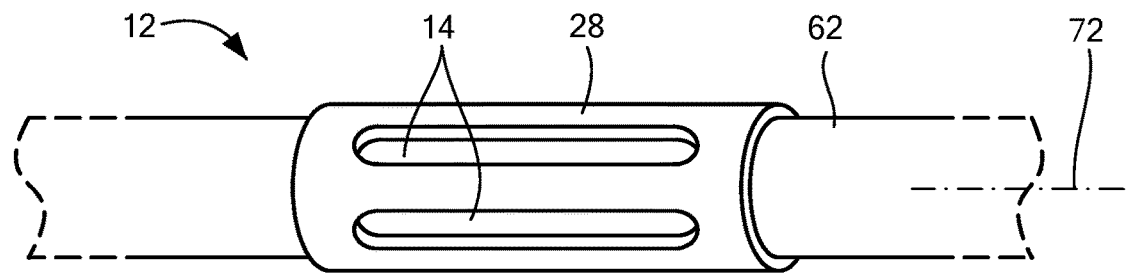
FIG. 10 shows a second embodiment of a band electrode having reverse irrigation ports.
Figure 11:
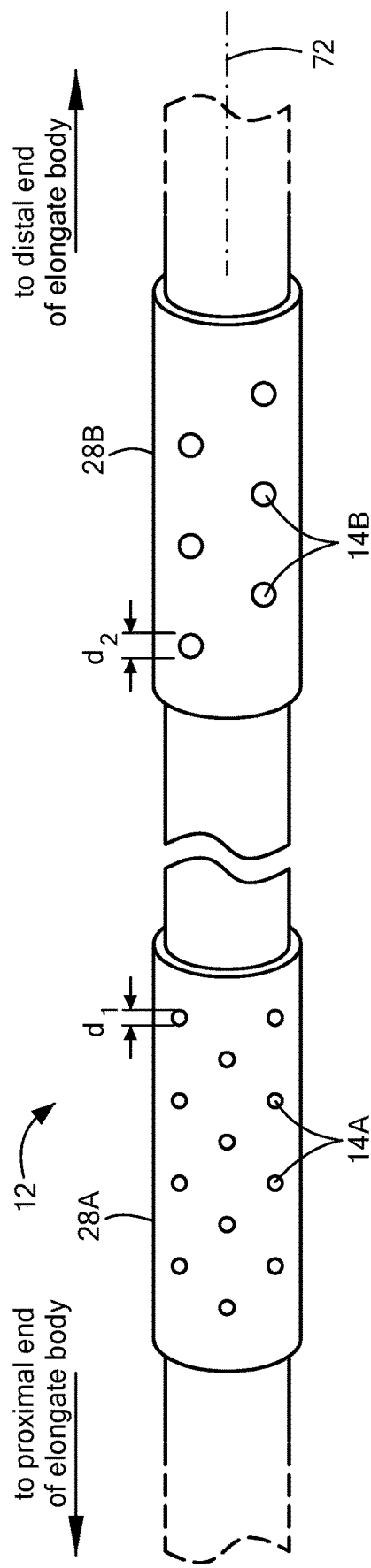
FIG. 11 shows a third embodiment of a band electrode having reverse irrigation ports.
Figure 12:
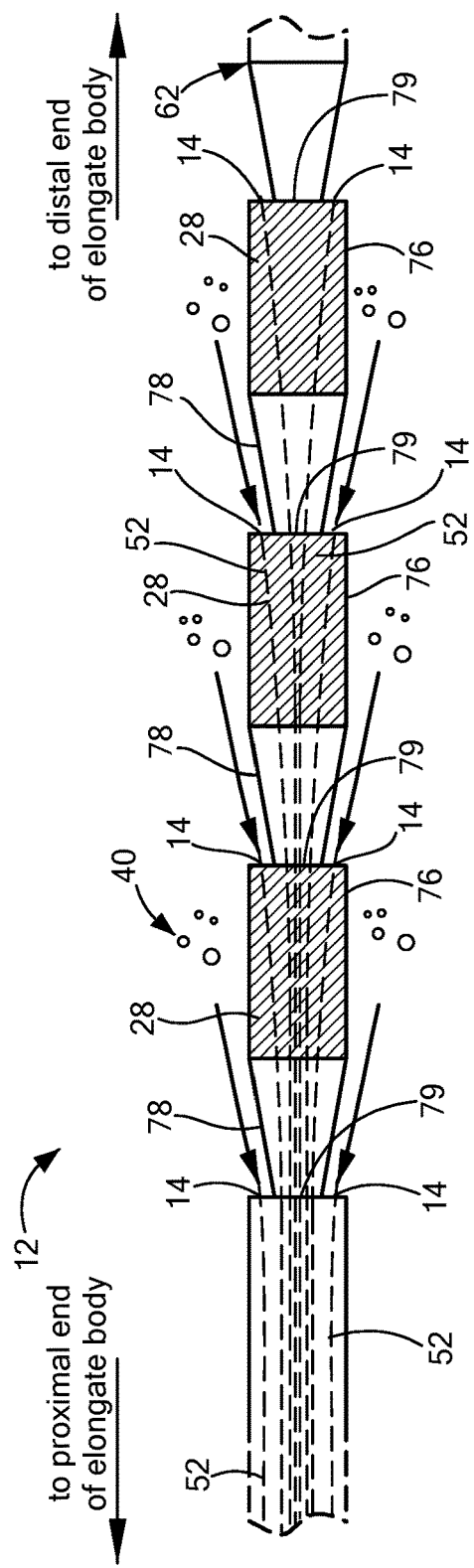
FIG. 12 shows a first embodiment of a reverse irrigation medical device having a distal portion with reverse irrigation ports and tapered segments.
Figure 13:
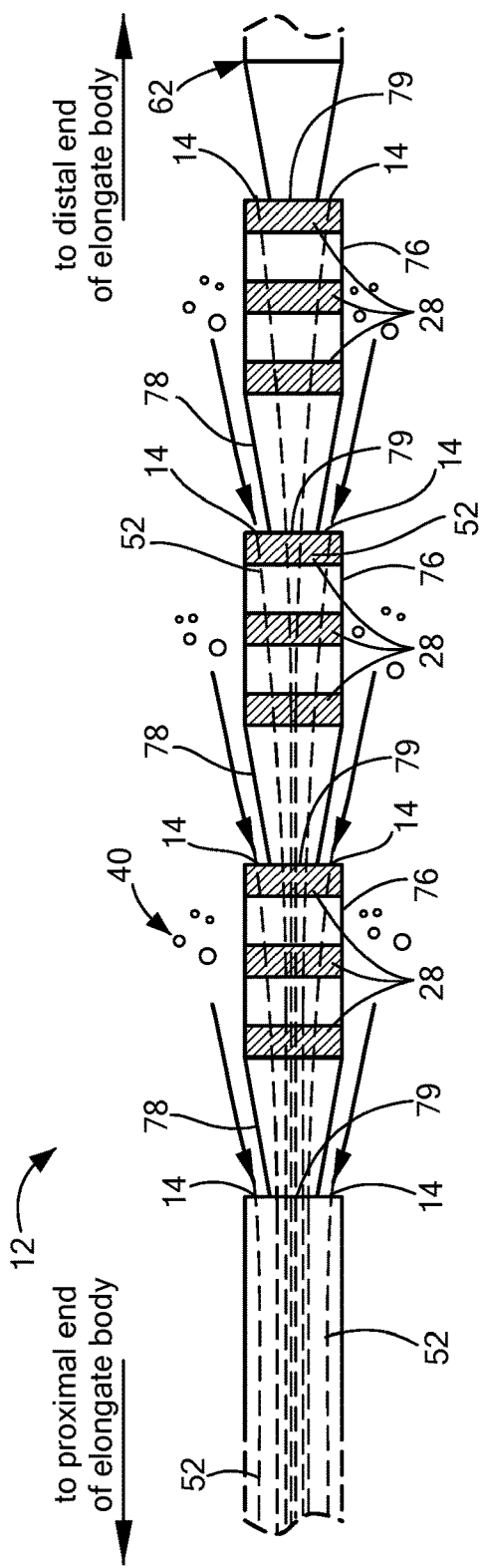
FIG. 13 shows a second embodiment of a reverse irrigation medical device having a distal portion with reverse irrigation ports and tapered segments.
Figure 29:
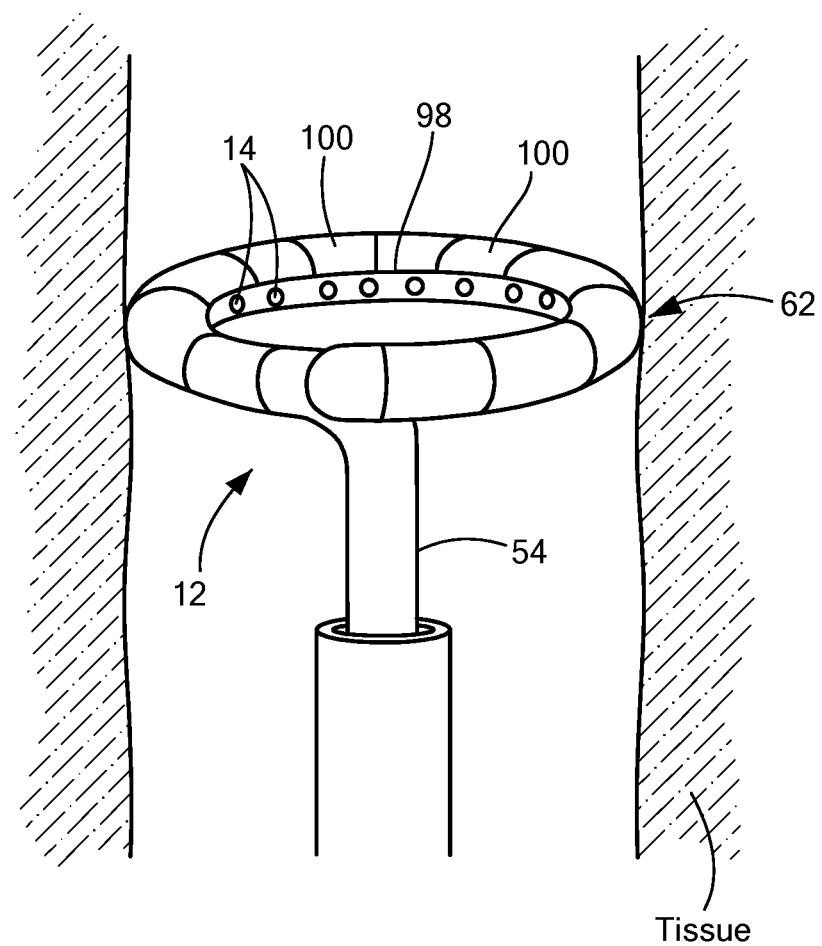
FIG. 29 shows the device of FIG. 28 with the distal portion of the device being in an exemplary expanded configuration.
Figure 30:
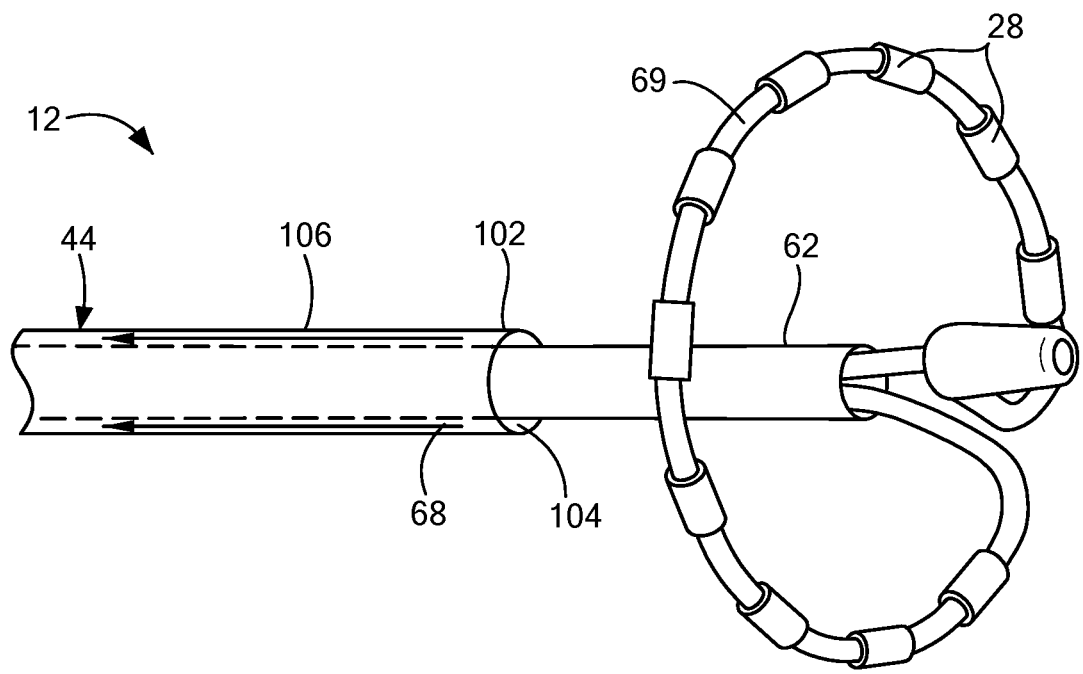
FIG. 30 shows a first embodiment of a device having a reverse irrigation sheath.
Figure 31:
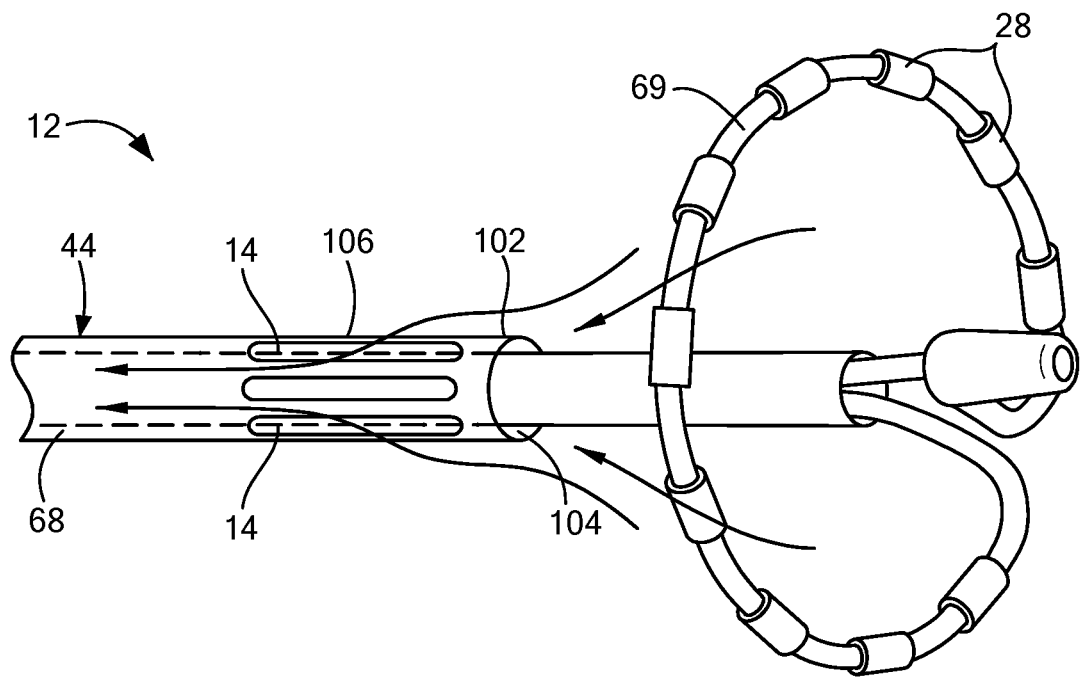
FIG. 31 shows a second embodiment of a device having a reverse irrigation sheath.

FIGS. 9-16 show embodiments of electrodes 28 along the distal portion 62 of the elongate body 54 of the reverse irrigation medical device 12 and reverse irrigation ports 14. Referring to FIGS. 9, 10, and 13, one or more band electrodes 28 may be affixed to, at least partially embedded within, deposited onto, incorporated into, or otherwise disposed on an outer or tissue-contacting surface of the distal portion 62 of the elongate body 54 of a reverse irrigation medical device 12. However, it will be understood that the electrodes 28 may have any other suitable configuration, even though band electrodes are shown. The electrodes 28 shown and discussed in FIGS. 9-16 may be located on the distal portion 62 of the elongate body 54 of a medical device 12 used for ablation, such as a focal catheter, or may be located on a segment of the elongate body 54 that is transitionable into an expanded or treatment configuration (for example, as shown in FIG. 29) or on a carrier arm 69 or array of a ablation elements of an ablation device (for example, as shown in FIGS. 30 and 31). Thus, the electrodes 28 shown in FIGS. 9-16 are located on the lateral walls of the distal portion of the elongate body 54, as opposed to being located at the distal end 64 of the elongate body 54 (for example, as shown in FIGS. 22-26). The medical device 12 may include a plurality of reverse irrigation ports 14, such that each electrode 28 includes or is proximate a portion of the plurality of reverse irrigation ports 14. In one embodiment, at least one band electrode may include one or more reverse irrigation ports 14 that extend from the outer surface of the band electrode to a reverse irrigation conduit within the elongate body. That is, each reverse irrigation port 14 is in fluid communication with at least one reverse irrigation conduit 52 and the environment surrounding the reverse irrigation medical device 12 (for example, the environment at the ablation site) so that the reverse irrigation system 18 may remove fluid from the environment and draw it through the medical device 12 to the waste removal system 22 and/or the fluid reclamation system 20.

Figure 17:
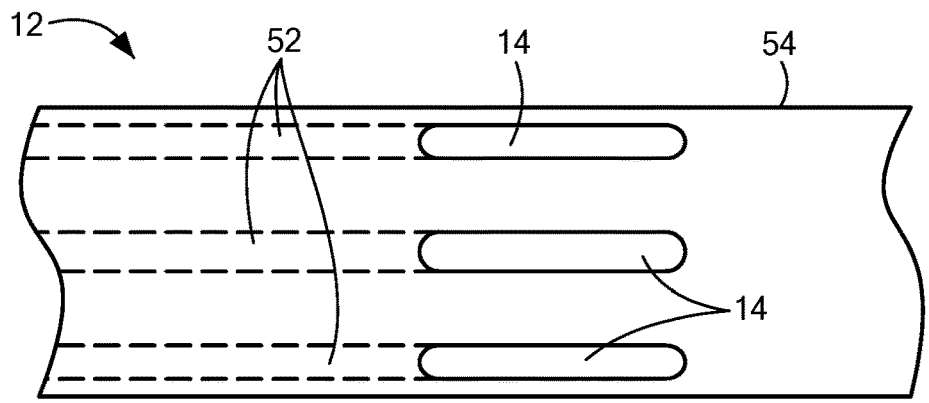
FIG. 17 shows a first configuration of reverse irrigation conduits.
Figure 18:
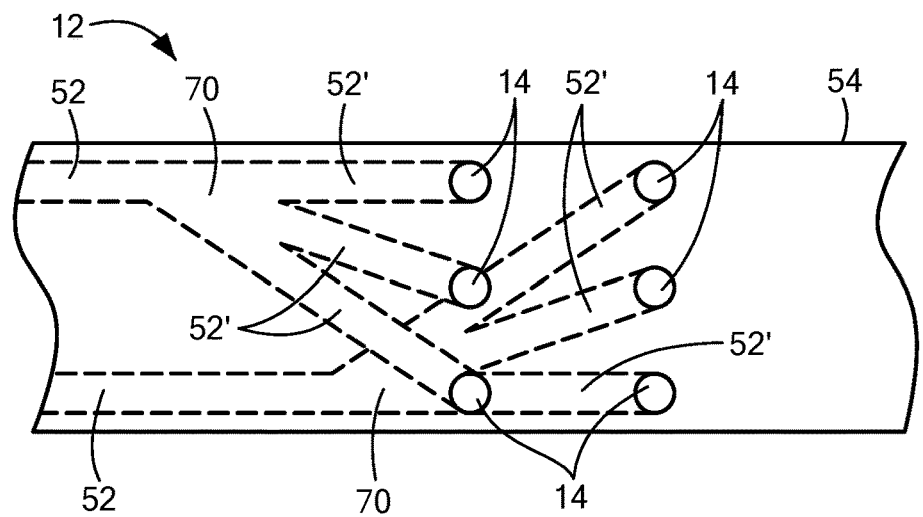
FIG. 18 shows a second configuration of reverse irrigation conduits.

Each reverse irrigation port 14 may be in fluid communication with a discrete reverse irrigation conduit 52 (for example, as shown in FIG. 17). This configuration may provide the added benefit of enabling the reverse irrigation medical device 12 to be held against or anchored to tissue by the suction of at least one of the reverse irrigation ports 14. This anchoring by suction may stabilize the medical device 12 at the ablation site and/or stabilize target tissue for ablation. Alternatively, a group of reverse irrigation ports 14 may be in fluid communication with a common reverse irrigation conduit 52 (for example, as shown in FIG. 18). In one embodiment, the medical device 12 may include at least one reverse irrigation conduit 52, the at least one reverse irrigation conduit 52 being branched 52' at a distal portion 70 and each branch 52' being in fluid communication with a single reverse irrigation port 14. In this configuration, each of the at least one reverse irrigation conduit 52 may be in fluid communication with a plurality of reverse irrigation ports 14. In either configuration, the proximal end of each reverse irrigation conduit (not shown) is connected to the reverse irrigation system 18 and waste removal system 22 and/or fluid reclamation system 20.

Figure 19:
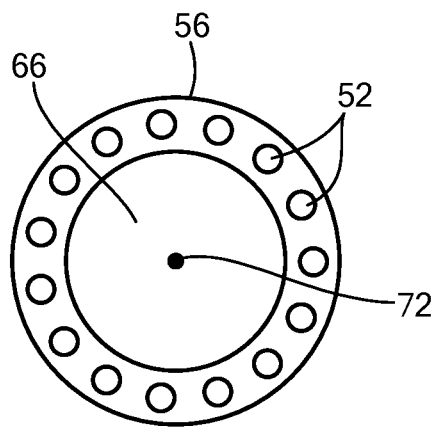
FIG. 19 shows a cross-section view of a first embodiment of a configuration of reverse irrigation conduits.
Figure 20:
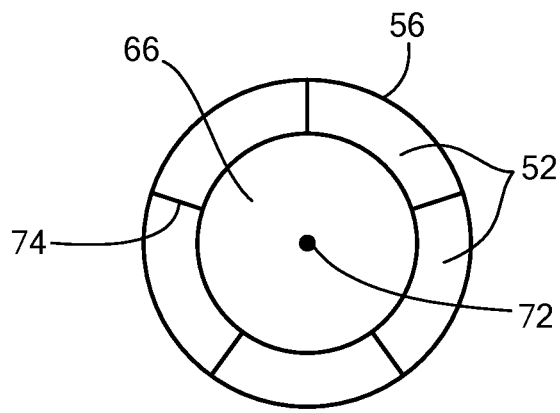
FIG. 20 shows a cross-section view of a second embodiment of a configuration of reverse irrigation conduits.
Figure 21:
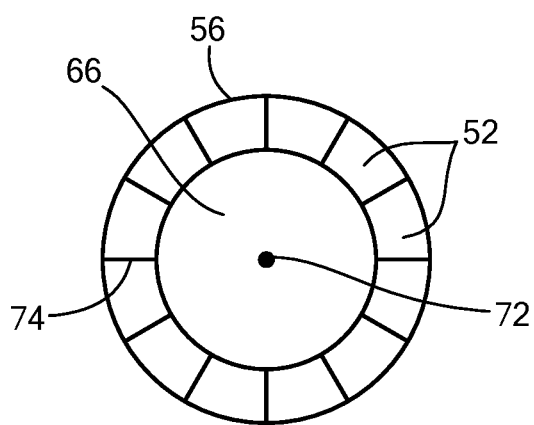
FIG. 21 shows a cross-section view of a third embodiment of a configuration of reverse irrigation conduits.

FIGS. 19-21 show cross-section views of the proximal portion 56 of the elongate body 54 of configurations of reverse irrigation conduits 52. Additionally, at least a portion of the distal portion 62 of the elongate body 54 may have the same configuration as the proximal portion 56 of the elongate body 54. As shown in FIG. 19-21, a plurality of reverse irrigation conduits 52 may be radially offset from and arranged around the elongate body longitudinal axis 72 (shown with a dot in the center of the elongate body 54 in FIGS. 19-21). In the embodiment shown in FIG. 19, each of the plurality of reverse irrigation conduits 52 may be symmetrically arranged around the elongate body longitudinal axis 72 and may be a distance from each adjacent reverse irrigation conduit 52. For example, each of the plurality of reverse irrigation conduits 52 may have a circular, or at least substantially circular, cross-sectional shape and may be circumferentially separated from each other within the wall of the elongate body 54 surrounding the central lumen 66 of the elongate body 54. Alternatively, as shown in FIGS. 20 and 21, each of the plurality of reverse irrigation conduits 52 may be immediately adjacent to each other and separated by radially arranged walls 74.

Referring again to FIGS. 9-16, at least one electrode 28, such as at least one band electrode, may include a plurality of reverse irrigation ports 14, such as a plurality of reverse irrigation ports 14 each having a circular, or at least substantially circular, shape (for example, as shown in FIG. 9). This configuration of reverse irrigation ports 14 may be referred to herein as having a circular shape for simplicity, although it will be understood that the shape may be oval, irregular, polyhedrous, square, or other non-elongate shape. Additionally or alternatively, at least one band electrode 28 may include a plurality of reverse irrigation ports 14, such as a plurality of reverse irrigation ports 14 each having an elongate shape, such as linear, at least substantially linear (for example, as shown in FIG. 10), curvilinear, spiral, or the like. In one embodiment, the elongate reverse irrigation ports 14 may be parallel to, or at least substantially parallel to, and radially offset from the elongate body longitudinal axis 72, and each elongate reverse irrigation port 14 may have a continuous width along its length. In another embodiment, the elongate reverse irrigation ports 14 may be arranged at an angle to the elongate body longitudinal axis 72 (not shown). The circular and/or elongate reverse irrigation ports 14 may be symmetrically arranged and/or arranged in a pattern on the electrode(s) or they may be randomly arranged on the electrode(s) 28.

In general, the total surface area of the reverse irrigation medical device 12 occupied by reverse irrigation ports 14 may be much larger than the total surface area of currently known non-irrigated ablation devices occupied by irrigation ports 14. In one embodiment, the total surface area of the medical device 12 occupied by the reverse irrigation ports 14 may be as much as 400% of the total surface area of the medical device 12 occupied by the electrodes 28. The reverse irrigation ports 14 shown in FIG. 9 may each have the same circular diameter (that is, the reverse irrigation ports 14 may all be the same size). In contrast, reverse irrigation ports 14 closer to the distal end 64 of the elongate body 54 may have a larger diameter than that of reverse irrigation ports 14 closer to the proximal end 58 of the elongate body 54. Further, the medical device 12 may include a larger number of reverse irrigation ports 14 closer to the distal end 64 of the elongate body 54. Put another way, reverse irrigation port 14 size and/or number may increase according to proximity to the elongate body distal end 64. This diameter increase may be gradual or the increase may be more stepped. In one embodiment, each electrode 28 may have a gradient or range of reverse irrigation port 14 diameters and/or numbers. For example, the diameter range may be between approximately 0.1 mm and approximately 1.5 mm. In another embodiment, a first electrode 28A may have a first plurality of circular reverse irrigation ports 14A all having the same first diameter $d_1$ and a distally adjacent second electrode 28B may have a second plurality of reverse irrigation ports 14B all having the same second diameter $d_2$, the second diameter $d_2$ being greater than the first diameter $d_1$ (for example, as shown in FIG. 11). Optionally, the second number of reverse irrigation ports 14B may also be greater than the first number of reverse irrigation ports 14A. Further, a distally adjacent third electrode 28 (not shown) may have a third plurality of reverse irrigation ports 14 all having the same third diameter, the third diameter being greater than the second diameter $d_2$ (and the third number may also be greater than the second number), and so on. The reverse irrigation port 14 diameters may increase slightly (for example, by approximately 10 μm) or more drastically (for example, by approximately 0.2 mm), and this increase may depend on device characteristics such as number of reverse irrigation ports 14, the length of the device over which the reverse irrigation ports 14 are distributed, the number of diameter increases, and the like. Additionally, not only the diameter but also the number of reverse irrigation ports 14 may increase in a proximal-to-distal direction. That is, an electrode 28 that is closest to the proximal end 58 of the elongate body 54 (for example, the first electrode 28A in FIG. 11) may include fewer reverse irrigation ports 14 than an electrode 28 that is closest to the distal end 64 of the elongate body 54 (for example, the second electrode 28B in FIG. 11). To compensate for increased size and/or number of reverse irrigation ports 14 closer to the distal end 64 of the elongate body 54, electrode size and/or number optionally may be greater closer to the distal end 64 of the elongate body 54.

Having reverse irrigation ports 14 with the greatest diameter located closer to the distal end 64 of the elongate body 54 may enhance efficiency of fluid removal by the reverse irrigation system 18. The farther away from the reverse irrigation system 18 a reverse irrigation port 14 is, the weaker the vacuum pull (or other fluid removal effect) exerted at that reverse irrigation port 14 will be. That is, the reverse irrigation ports 14 located closest to the proximal end 58 of the elongate body 54 may exert a stronger pull on, and therefore may be more efficient at removing, fluid at the ablation site than the pull exerted on fluid at the ablation site by reverse irrigation ports 14 located closest to the distal end 64 of the elongate body 54. To compensate for this effect, the larger reverse port 14 irrigation diameter may allow the more distal reverse irrigation ports 14 to remove a comparable amount of, or more, fluid than the more proximal reverse irrigation ports 14 having a smaller diameter.

Figure 14:
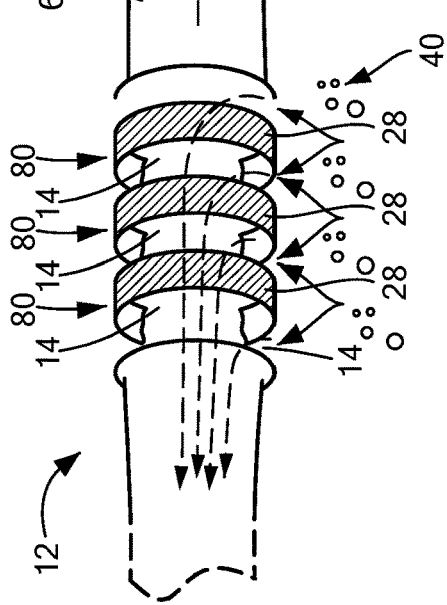
FIG. 14 shows an embodiment of a reverse irrigation medical device having a distal portion with reverse irrigation ports and electrode segments.

FIGS. 12-14 show reverse irrigation medical device 12 embodiments that include one or more reverse irrigation ports 14 that extend around an entirety of, or at least a portion of, or are distributed around the a circumference of the distal portion 62 of the elongate body 54. In one embodiment, the distal portion 62 of the elongate body 54 may include one or more generally cone-shaped segments. In one embodiment, each of the cone-shaped segments includes a segment 76 having a continuous diameter. The continuous diameter may be the same or substantially the same as the continuous diameter of the proximal portion 56 of the elongate body 54 and/or non-segmented portions of the distal portion 62 of the elongate body 54. Each segment 76 having a continuous diameter may include one (for example, as shown in FIG. 12) or a plurality (for example, as shown in FIG. 13) of ablation elements, such as band electrodes or electrodes of other configurations. Further, each of the segments 76 having a continuous diameter, and the portion of the elongate body 54 that is immediate proximal to the most proximal cone-shaped segment, may have a distal surface that each includes one or more reverse irrigation ports 14.

Each of the cone-shaped segments may further include a tapered segment 78 that is located immediately adjacent to each segment 76 having a continuous diameter. In one embodiment, the taper is a gradually decreasing diameter of the elongate body 54 in a distal-to-proximal direction. Each tapered segment 78 may be in fluid communication with, and may be configured to draw fluid into, one or more reverse irrigation conduits 52 within the elongate body 54. This configuration may facilitate fluid draw into the reverse irrigation ports 14, as fluid may more readily flow into the reverse irrigation ports 14 at an angle other than 90 degrees. Further, this configuration may cause the fluid draw to flow over the electrodes 28, providing a cooling effect to the electrodes 28. In one embodiment, the diameter at the smaller end of the tapered segment 78 may be only slightly larger the diameter of the central lumen 66 (for example larger by a thickness of the material used to form the elongate body and/or the smaller end of the tapered segment 78). Additionally, radial supports for the cone-shaped segments optionally may be included.

As shown in FIG. 14, the reverse irrigation medical device 12 may include a plurality of ablation segments 80 having a first diameter and adjacent non-ablation segments 82 having a second diameter that is less than the first diameter. Each ablation segment 80 may include at least one ablation element 28, such as a band electrode. In one embodiment, a plurality of reverse irrigation ports 14 may radially extend outward from one or more reverse irrigation conduits 52 through the elongate body wall. Further, such a plurality of reverse irrigation conduits 14 may be included on either side of the ablation segments 80. Put another way, each ablation segment 80 may be formed by virtue of the pluralities of reverse irrigation ports 14.

Figure 15:
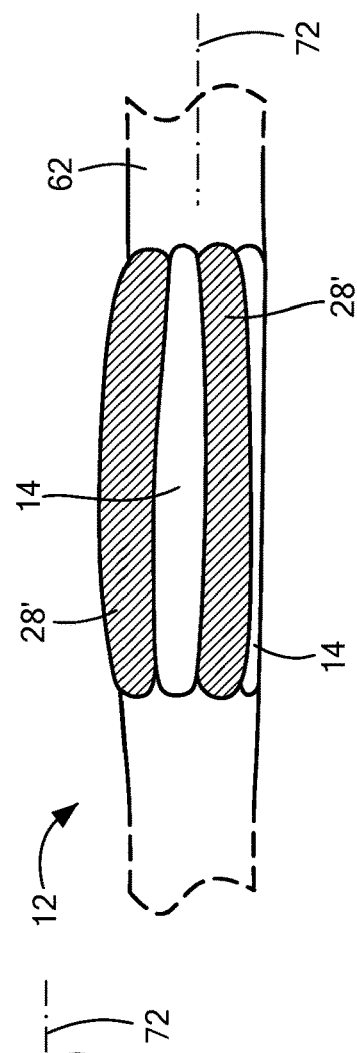
FIG. 15 shows a first embodiment of linear electrodes being alternated with reverse irrigation ports.
Figure 16:
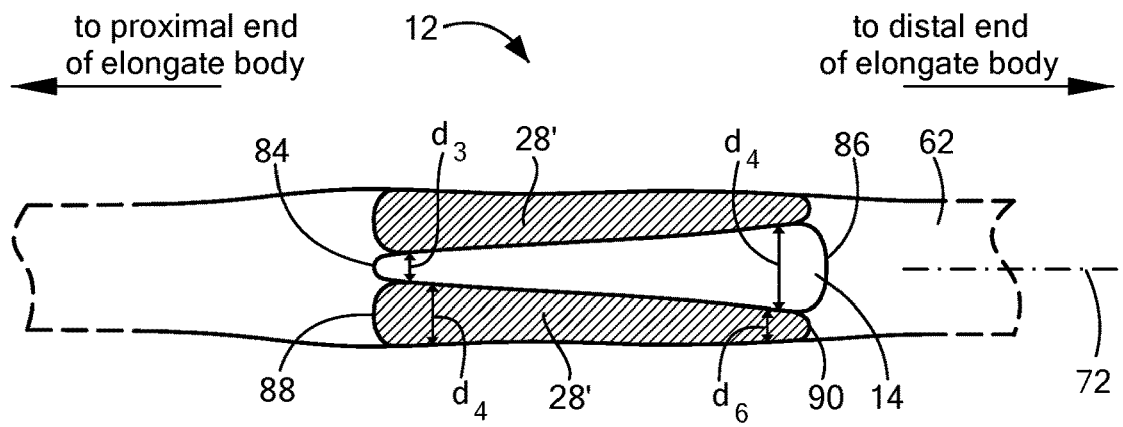
FIG. 16 shows a second embodiment of linear electrodes being alternated with reverse irrigation ports.

Referring to FIGS. 15 and 16, the reverse irrigation medical device 12 may include a plurality of elongate electrodes 28' affixed to, at least partially embedded within, deposited onto, incorporated into, or otherwise disposed on an outer or tissue-contacting surface of the distal portion 62 of the elongate body 54. In one embodiment, the elongate electrodes 28' may each have a shape that is linear, at least substantially linear, curvilinear, or the like. The plurality of elongate electrodes 28' may be arranged parallel to and radially offset from the elongate body longitudinal axis 72, and may be alternated with a plurality of elongate reverse irrigation ports 14. In contrast to the embodiment shown in FIG. 10 in which the reverse irrigation ports 14 may be apertures within an electrode 28, in the embodiments shown in FIGS. 15 and 16, the reverse irrigation ports 14 may be apertures within the elongate body 54 and may be located between adjacent electrodes 28'. In one embodiment, each of the elongate reverse irrigation ports 14 and each of the elongate electrodes 28' may be parallel to and radially offset from the elongate body longitudinal axis 72 and each of the elongate reverse irrigation ports 14 and each of the elongate electrodes 28' may have a continuous width along its length (for example, as shown in FIG. 15). In another embodiment, each of the elongate reverse irrigation ports 14 may each have a tapered shape with an increasing diameter in a proximal-to-distal direction (for example, as shown in FIG. 16). That is, the proximal end 84 of each elongate reverse irrigation port 14 may have a diameter $d_3$ that is less than the diameter $d_4$ of the distal end 86 of the elongate reverse irrigation port 14. Conversely, the elongate electrodes 28' located between the elongate reverse irrigation ports 14 may each have a tapered shape with a decreasing diameter in a proximal-to-distal direction. That is, the proximal end 88 of each elongate electrode 28' may have a diameter $d_5$ that is greater than the diameter $d_6$ of the distal end 90 of the elongate electrode 28', such that each elongate reverse irrigation port 14 abuts or is immediately adjacent each of two adjacent elongate electrodes 28'. As discussed above, the proximal-to-distal increasing diameter of each elongate reverse irrigation port 14 may compensate for the reduced suction or pull on fluid at the distal end 86 of each elongate reverse irrigation port 14 compared to that of the proximal end 84 of each elongate reverse irrigation port 14. In either configuration, each elongate electrodes 28' may be immediately adjacent at least one elongate reverse irrigation port 14.

Figure 22:
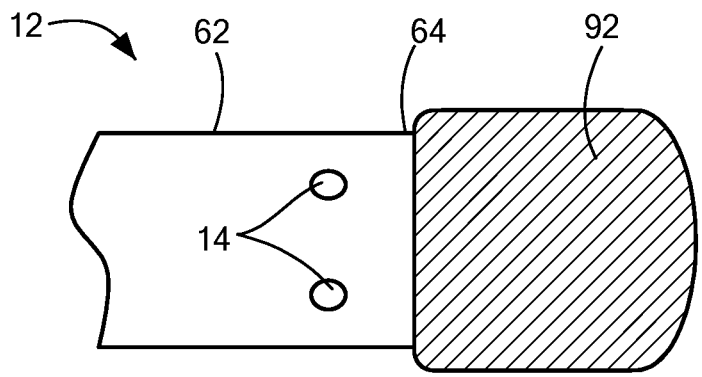
FIG. 22 shows a first embodiment of a distal portion of a reverse irrigation medical device.
Figure 23:
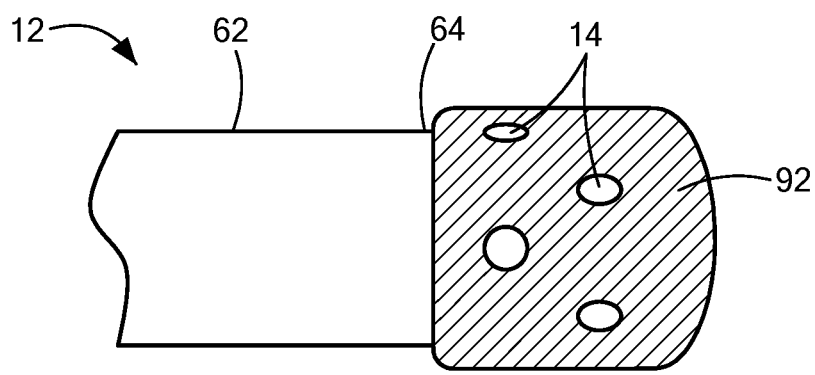
FIG. 23 shows a second embodiment of a distal portion of a reverse irrigation medical device.
Figure 24:
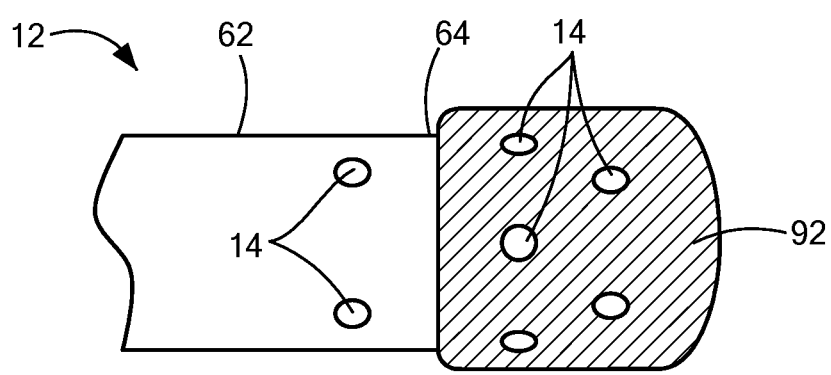
FIG. 24 shows a third embodiment of a distal portion of a reverse irrigation medical device; shows a fifth embodiment of a distal portion of a reverse irrigation medical device.

Referring now to FIGS. 22-24, three general embodiments of a distal portion of a reverse irrigation medical device 12 are shown. The distal portion 62 of the elongate body 54 may include a distal end 64 having a distal tip electrode 92 that is affixed to, at least partially embedded within, deposited onto, incorporated into, or otherwise disposed on an outer or tissue-contacting surface of the distal end 64 of the elongate body 54 such that the distal tip electrode 92 defines a distal-most surface of the medical device 12. The distal tip electrode 92 may be an ablation element. In one embodiment, one or more reverse irrigation ports 14 may be included in the distal portion 62 of the elongate body 54, proximal to and proximate the distal tip electrode 92 (for example, as shown in FIG. 22). In another embodiment, one or more reverse irrigation ports 14 may be included in the distal tip electrode 92 (for example, as shown in FIG. 23). In yet another embodiment, one or more reverse irrigation ports 14 may be included not only on the distal tip electrode 92, but also in the distal portion 62 of the elongate body 54 proximal to and proximate the distal tip electrode 92 (for example, as shown in FIG. 24).

Figure 25:
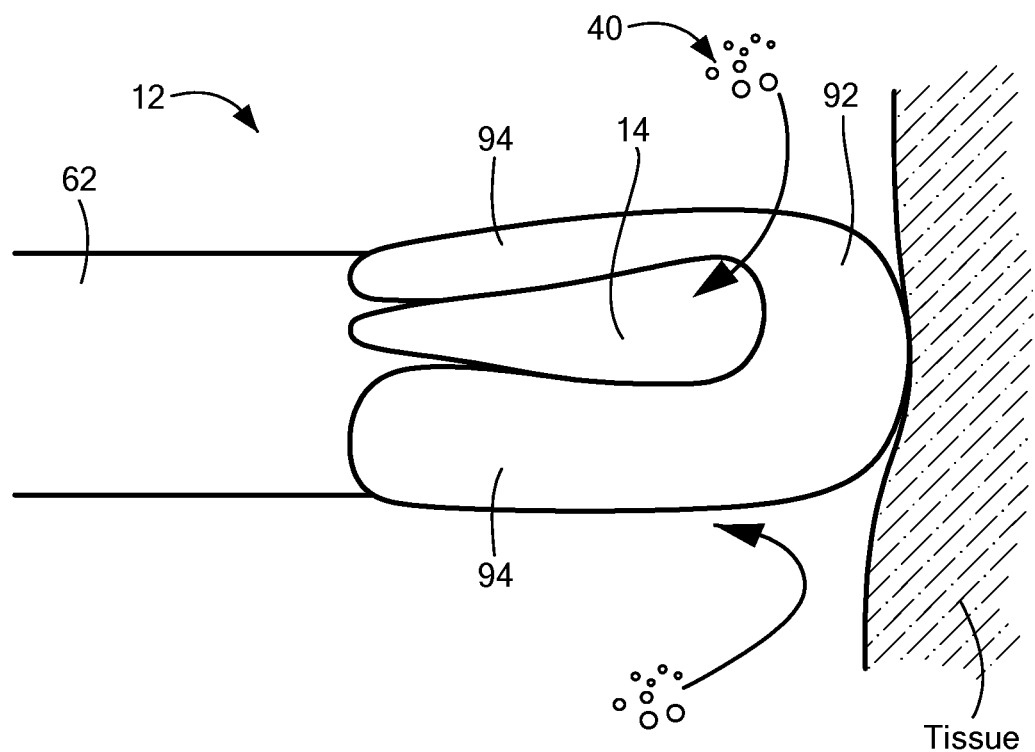
FIG. 25 shows a first embodiment of a distal portion of a reverse irrigation medical device having a distal tip electrode with reverse irrigation.
Figure 26:
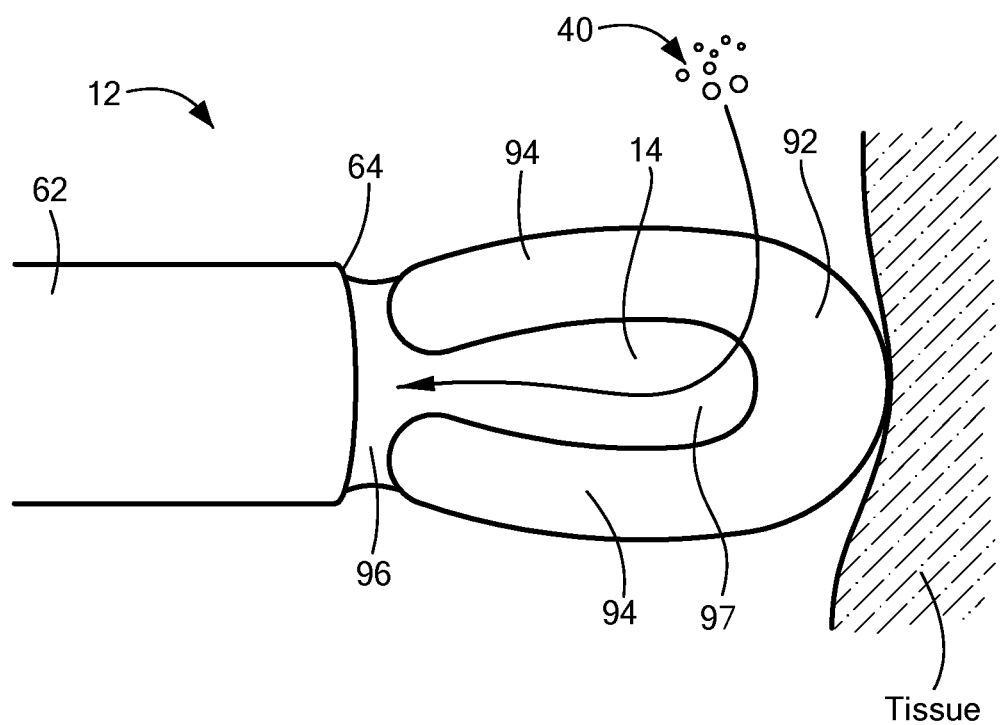
FIG. 26 shows a second embodiment of a distal portion of a reverse irrigation medical device having a distal tip electrode with reverse irrigation.

FIGS. 25 and 26 show embodiments of an elongate body distal portion 62 with reverse irrigation ports 14. The distal tip electrode 92 may be configured such that the distalmost surface of the distal tip electrode 92 is configured to deliver thermal and/or electrical energy to an area of tissue or, in the case of cryotreatment, to remove heat from the area of tissue. Thus, the distalmost surface of the distal tip electrode 92 may not include any reverse irrigation ports 14. The distal tip electrode 92 may include one or more elongated portions 94 that each extends in a direction parallel, or at least substantially parallel, to the elongate body longitudinal axis 72 and toward the proximal end 58 of the elongate body 54. As shown in FIG. 25, the distal tip electrode 92 may further include a plurality of elongated reverse irrigation ports 14, with the elongated reverse irrigation ports 14 alternating with the elongated portions 94 of the distal tip electrode 92 around the circumference of the elongate body distal portion 62. The elongated reverse irrigation ports 14 and the elongated portions 94 of the distal tip electrode 92 may each be tapered in a complementary configuration. In this configuration, fluid may be drawn from the ablation site over the distal tip electrode 92 and into the plurality of elongated reverse irrigation ports 14. As shown in FIG. 26, the distal tip electrode 92 may include a neck portion 96 that has a diameter than is less than a diameter of the distal portion 62 of the elongate body 54. Further, the distal end 64 of the elongate body 54 may include distal surface that defines one or more reverse irrigation ports 14. The portions of the reverse irrigation port(s) 14 that are between the elongated portions 94 of the distal tip electrode 92 may not be apertures, but may instead be non-conductive contoured areas 97 to channel fluid from the ablation site into the portions of the reverse irrigation ports 14 defining an opening within the distal end 64 of the elongate body.

Figure 27:
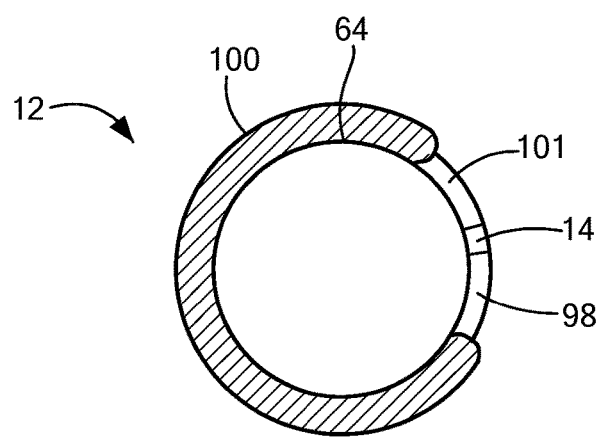
FIG. 27 shows a cross-section view of a distal portion of a device having an elongate reverse irrigation band.
Figure 28:
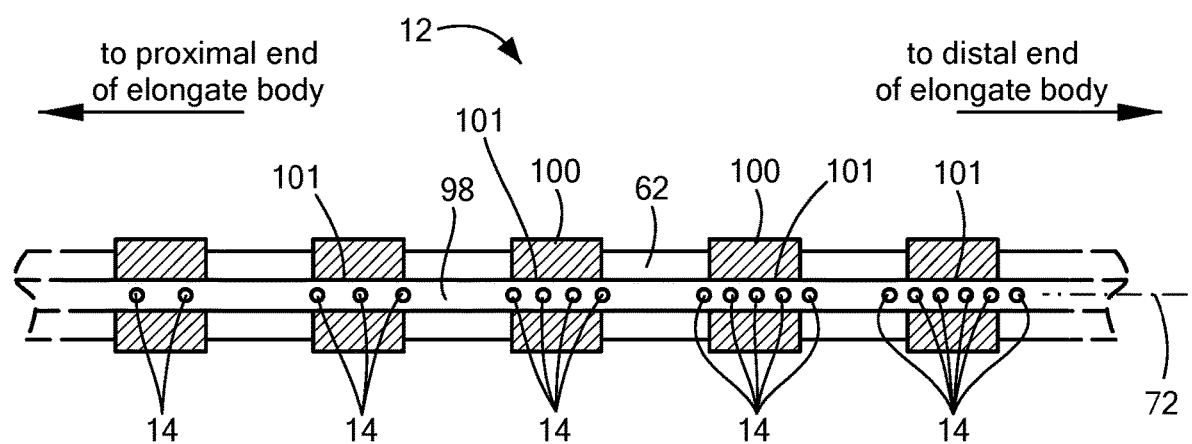
FIG. 28 shows a portion of the device of FIG. 25 having an elongate reverse irrigation band.

Referring now to FIGS. 27-29, a reverse irrigation medical device 12 having an elongate reverse irrigation band 98 is shown. The medical device 12 may be an ablation device having an elongate configuration, such as a focal catheter. Optionally, the medical device 12 may be transitionable between a first linear configuration and a second expanded configuration, such as when the distal portion 62 of the elongate body 54 of the medical device 12 is transitioned into a loop, hoop, or curvilinear shape (for example, as shown in FIG. 29).

In general, the reverse irrigation medical device 12 may include a plurality of electrodes 100 that extend around a portion of the circumference of the elongate body 54, such that a strip remains on at least one surface of the elongate body 54 in which the electrodes 100 are not located. The electrodes 100 may be ablation elements. For example, as shown in FIG. 27, each of a plurality of electrodes 100 may be an arcuate electrode that extends around less than the entire circumference of the distal portion 62 of the elongate body 54 such that each electrode 100 defines a gap 101. In one embodiment, each electrode 100 may extend between approximately 50% and approximately 85% of the circumference of the distal portion 62 of the elongate body 54. This may leave a strip of the elongate body 54 that is parallel to, or at least substantially parallel to, the elongate body longitudinal axis 72 that does not include a portion of each electrode (that is, a linear non-conductive area on the distal portion 62 of the elongate body 54). The distal portion 62 may also include an elongate band 98 composed of a material that is not electrically and/or thermally transmissive. This elongate band 98 may be parallel to, or at least substantially parallel to, the elongate body longitudinal axis 72, and may extend along at least a portion of the linear non-conductive area on the distal portion 62 of the elongate body 54, within the gaps 101 of the electrodes 100. Further, the elongate band 98 may extend along a distance that is at least as long as the distance over which the plurality of electrodes 100 extend.

The elongate band 98 may include a plurality of reverse irrigation ports 14. In one embodiment, the plurality of reverse irrigation ports 14 may be evenly spaced and may extend along the entire, or at least substantially the entire, length of the elongate band 98. In another embodiment, although the plurality of reverse irrigation ports 14 may extend along the entire, or least substantially the entire, length of the elongate band 98, the reverse irrigation ports 14 may be clustered into groups that are aligned with each of the plurality of electrodes 100 (for example, as shown in FIG. 26). Further, the number and/or diameter of reverse irrigation ports 14 may increase in a proximal-to-distal direction, for example as disclosed above regarding FIG. 13.

In one embodiment, the elongate reverse irrigation band 98 may be positioned on the elongate body 54 such that the elongate reverse irrigation band 98 is located on the non-tissue-contact surface of the distal portion 62 of the elongate body 54, and the electrodes 100 are located on the tissue-contact surfaces of the distal portion 62 of the elongate body 54, when the medical device 12 is in the second expanded configuration (for example, as shown in FIG. 29, the distal portion 62 of the elongate body being within a vessel, such as a pulmonary vein). Thus, when the elongate body 54 is in the expanded second configuration and used to ablate tissue, the elongate reverse irrigation band 98 is located on the inside of the loop configuration and does not interfere with ablation of the tissue, but is also located such that the reverse irrigation ports 14 may remove fluid from the ablation site.

Referring now to FIGS. 30-35, embodiments of a reverse irrigation medical device 12 including reverse irrigation sheath 44 are shown. In general, the medical device may 12 include an ablation device 42 and a reverse irrigation sheath 44. The reverse irrigation sheaths 44 shown in FIGS. 30-35 may be in fluid communication with the reverse irrigation system 18 and waste removal system 22 and/or the fluid reclamation system 20. However, it will be understood that the ablation device 42 may or may not be in fluid communication with the reverse irrigation system 18 and waste removal system 22 and/or the fluid reclamation system 20.

As shown in FIG. 30, the reverse irrigation sheath 44 may not include reverse irrigation ports 14 extending through the wall of the reverse irrigation sheath 44; however, the reverse irrigation sheath 44 may include a central lumen 68 and a distal end 102 with a distal opening 104 that is in communication with the sheath central lumen 68 and functions as a reverse irrigation port 14 (and, therefore, which may be referred to herein as a reverse irrigation port 14). In one embodiment, the ablation device 42 may be extendable through the distal opening 104 at the distal end 102 of the reverse irrigation sheath 44, and the fluid may be removed from the ablation site through the distal opening 104.

Alternatively, as shown in FIGS. 31-35, the reverse irrigation sheath 44 may include a distal portion 106 with a distal end 102 having an opening 104 and one or more reverse irrigation ports 14 in the wall of the sheath distal portion 106. The ablation device 42 may be extendable through the distal opening 104 at the distal end 102 of the reverse irrigation sheath 44, and fluid may be removed from the ablation site through both the distal opening 104 and the one or more reverse irrigation ports 14. In one embodiment, the one or more reverse irrigation ports 14 may be in fluid communication with the central lumen 68 of the reverse irrigation sheath 44 (that is, the lumen 68 through which the ablation device 42 is extendable). In this configuration, the vacuum pump 32 (or other fluid removal components) of the reverse irrigation system 18 may be in fluid communication with, and fluid passed to the waste removal system 22 and/or fluid reclamation system 20 through, the central lumen 68 of the reverse irrigation sheath 44. In another embodiment, the one or more reverse irrigation ports 14 may be in fluid communication with one or more reverse irrigation conduits 52 within the reverse irrigation sheath wall or central lumen 68. In this configuration, the vacuum pump 32 (or other fluid removal components) of the reverse irrigation system 18 may be in fluid communication with, and fluid passed to the waste removal system 22 and/or fluid reclamation system 20 through, the reverse irrigation ports 14 and, optionally, the central lumen 68 of the reverse irrigation sheath 44.

Figure 32:
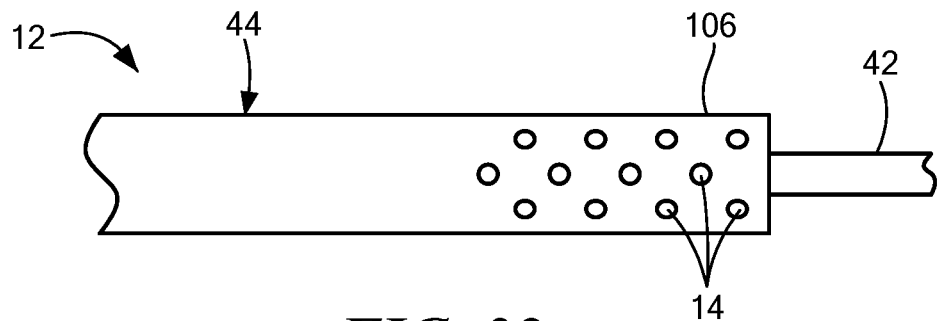
FIG. 32 shows a third embodiment of a device having a reverse irrigation sheath.
Figure 33:
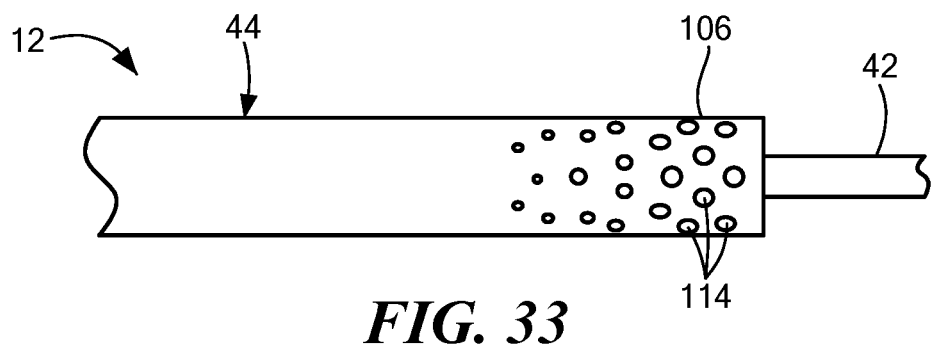
FIG. 33 shows a fourth embodiment of a device having a reverse irrigation sheath.

As shown in FIG. 31, the sheath distal portion 106 may include a plurality of elongate reverse irrigation ports 14 that each extends from the outer surface of the reverse irrigation sheath 44 to the reverse irrigation sheath central lumen 68 and/or to one or more reverse irrigation conduits 52. Optionally, fluid from the ablation site may be drawn into the reverse irrigation sheath central lumen 68 through the sheath distal opening 104 as well as being drawn into the plurality of elongate reverse irrigation ports 14 in the wall of the reverse irrigation sheath 44. As shown in FIGS. 32 and 33, the reverse irrigation sheath 44 may include a plurality of reverse irrigation ports 14 in the wall of the reverse irrigation sheath 44, and each reverse irrigation port 14 may have a circular, or at least substantially circular, shape. The reverse irrigation ports 14 may be organized into a symmetrical pattern (as shown in FIG. 32) or may be randomly distributed in the wall of the reverse irrigation sheath. Further, each of the plurality of reverse irrigation ports 14 may have a diameter, and the number and/or diameter of the plurality of reverse irrigation ports 14 may decrease in a distal-to-proximal direction as discussed above regarding, for example, FIG. 13. For example, reverse irrigation ports 14 being farther from the distal end 64 of the elongate body 54 (that is, closer to the proximal end 58 of the elongate body 54) may each have a diameter that is less than a diameter of reverse irrigation ports 14 that are closer to the distal end 64 of the elongate body 54.

Figure 34:
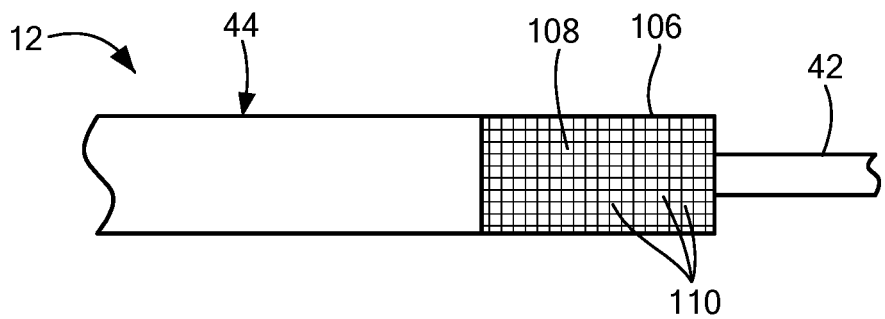
FIG. 34 shows a fifth embodiment of a device having a reverse irrigation sheath.

As shown in FIG. 34, the distal portion 105 of the reverse irrigation sheath 44 may include a mesh 108 or other fluid permeable material. In one embodiment, the reverse irrigation sheath 44 may include a mesh 108 of interwoven fibers or other configuration of material having a plurality of apertures 110 (referred to herein as a mesh 108). The mesh 108 may be coupled to or affixed to the distal end 102 of the reverse irrigation sheath 44 such that the mesh 108 defines the distal opening 104 of the reverse irrigation sheath 44. Alternatively, the distal portion 106 of the reverse irrigation sheath 44 itself may be laser cut, perforated, aperture, or otherwise include a plurality of openings or apertures 110 configured to allow fluid to be drawn from the ablation site into the reverse irrigation sheath central lumen 68 and/or into one or more reverse irrigation conduits 52 within the reverse irrigation sheath 44. Thus, the mesh 108 having a plurality of apertures 110 may be referred to herein as a reverse irrigation port 14.

Figure 35:
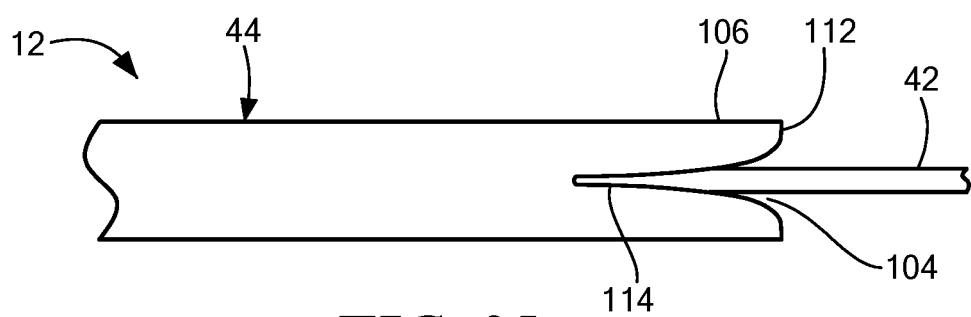
FIG. 35 shows a sixth embodiment of a device having a reverse irrigation sheath.

As shown in FIG. 35, the reverse irrigation sheath distal portion 106 may be configured such that the distal opening 104 of the reverse irrigation sheath 44 is scalloped or undulating. In one embodiment, the reverse irrigation sheath distal portion 106 may include a plurality of undulations, for example, three or more. As for the reverse irrigation sheath 44 shown in FIG. 30, the reverse irrigation sheath of FIG. 35 may not include any reverse irrigation ports 14 extending through the wall of the reverse irrigation sheath 44, but the distal opening 104 that is in communication with the sheath central lumen 68 may function as a reverse irrigation port 14 (and, therefore, may be referred to herein as a reverse irrigation port 14). This configuration may provide a similar function to the reverse irrigation port 14 diameter gradient discussed above. That is, the distalmost portion 112 of the reverse irrigation sheath distal opening 104 may provide a larger area through which fluid may be drawn from the ablation site, whereas the narrowed openings formed by the more proximal portions 114 of the reverse irrigation sheath distal opening 104 may provide a smaller area through which fluid may be drawn from the ablation site. This may compensate for the reduced fluid draw produced by the vacuum pump 32 (or other fluid removal component) of the reverse irrigation system 18 at the distalmost portions 112 of the reverse irrigation sheath distal opening 104.

The reverse irrigation devices described herein may be used with currently existing irrigation systems. In that case, the irrigation system may be in communication with the reverse irrigation system 18 and/or may be operated independently of the reverse irrigation system 18. Further, the reverse irrigation system 18 and an irrigation system may be in communication with a common ablation device. In one embodiment, an ablation device 12 such as those described herein may be in fluid communication with both a reverse irrigation system 18 and an irrigation system, such that the reverse irrigation conduit(s) 52 of the device 12 may be used to deliver irrigation fluid to an ablation site and withdraw fluid from the ablation site. In one embodiment, an ablation device may be used to deliver radiofrequency energy and/or electroporation energy, irrigation fluid may be delivered through the reverse irrigation ports 14 to cool the ablation electrodes and fluid from the treatment site may also be withdrawn through the reverse irrigation ports 14 by the reverse irrigation system 18. The fluid delivery and withdrawal may occur simultaneously (for example, some of the reverse irrigation ports 14 may be used to deliver irrigation fluid, whereas other reverse irrigation ports 14 may be used to withdraw fluid from the ablation site), sequentially (for example, periods of irrigation fluid delivery alternated with periods of fluid withdrawal), and/or independently initiated manually or semi-automatically at the user's discretion before, during, and/or after the procedure.

In one embodiment, a reverse irrigation device 12 comprises at least one ablation electrode 28/92 and at least one reverse irrigation port 14, the at least one reverse irrigation port 14 being located at at least one of immediately proximate the at least one ablation electrode 28/92 and on the at least one ablation electrode 28/92, the at least one reverse irrigation port 14 being configured to be in fluid communication with a fluid removal component 32.

In one aspect of the embodiment, the at least one reverse irrigation port 14 is on the at least one ablation electrode 28/92.

In one aspect of the embodiment, the at least one reverse irrigation port 14 has an at least substantially circular shape.

In one aspect of the embodiment, the at least one reverse irrigation port 14 has an elongate shape.

In one aspect of the embodiment, the reverse irrigation device 12 further comprises an elongate body 54 having a distal portion 62, a proximal portion 56 opposite the distal portion 62, and a longitudinal axis 72, the at least one ablation element 28 including a plurality of ablation electrodes 28 on the elongate body distal portion 62 and the at least one reverse irrigation port 14 including a plurality of reverse irrigation ports 14.

In one aspect of the embodiment, the plurality of ablation electrodes 28 includes a first ablation electrode 28A and a second ablation electrode 28B located distal to the first ablation electrode 28A; and the first ablation electrode 28A includes a first plurality of reverse irrigation ports 14A and the second ablation electrode 28B includes a second plurality of reverse irrigation ports 14B.

In one aspect of the embodiment, each of the first plurality of reverse irrigation ports 14A has a first diameter $d_1$ and each of the second plurality of reverse irrigation ports 14B has a second diameter $d_2$ that is greater than the first diameter $d_1$.

In one aspect of the embodiment, the first plurality of reverse irrigation ports 14A includes a first number of reverse irrigation ports 14A and the second plurality of reverse irrigation ports 14B includes a second number of reverse irrigation ports 14B that is greater than the first number of reverse irrigation ports 14A.

In one aspect of the embodiment, at least one of the first plurality of reverse irrigation ports 14A has a first diameter $d_1$ and at least one of the second plurality of reverse irrigation ports 14B has a second diameter $d_2$ that is greater than the first diameter $d_1$.

In one aspect of the embodiment, the first plurality of reverse irrigation ports 14A includes a first number of reverse irrigation ports 14A and the second plurality of reverse irrigation ports 14B includes a second number of reverse irrigation ports 14B that is greater than the first number of reverse irrigation ports 14A.

In one aspect of the embodiment, the at least one reverse irrigation port 14 is immediately adjacent the at least one ablation electrode 28.

In one aspect of the embodiment, the reverse irrigation device 12 further comprises: an elongate body 54 having a distal portion 62, a proximal portion 56 opposite the distal portion 62, and a longitudinal axis 72; the at least one ablation element 28 including a plurality of elongate ablation electrodes 28' on the elongate body distal portion 62, the plurality of elongate ablation electrodes 28' being radially offset from and parallel to the elongate body longitudinal axis 72; and the at least one reverse irrigation port 14 including a plurality of elongate reverse irrigation ports 14 being alternated with the plurality of elongate ablation electrodes 28', the plurality of elongate reverse irrigation ports 14 being radially offset from and parallel to the elongate body longitudinal axis 72.

In one aspect of the embodiment, each of the elongate reverse irrigation ports 14 has a proximal end 84 and a distal end 86, each of the elongate reverse irrigation ports 14 being tapered such that the reverse irrigation port proximal end 84 has a first diameter $d_3$ and the reverse irrigation port distal end 86 has a second diameter $d_4$ that is greater than the first diameter $d_3$ of the reverse irrigation port proximal end 84; and each of the elongate ablation electrodes 28' has a proximal end 88 and a distal end 90, each of the elongate ablation electrodes 28' being tapered such that the ablation electrode proximal end 88 has a first diameter $d_5$ and the ablation electrode distal end 90 has a second diameter $d_6$ that is less than the first diameter $d_5$ of the ablation electrode proximal end 88.

In one aspect of the embodiment, the reverse irrigation device 12 further comprises: an elongate body 54 having a distal portion 62, a proximal portion 56 opposite the distal portion 62, a longitudinal axis 72, and a circumference, the at least one ablation electrode 28 including a plurality of arcuate electrodes 100, each of the plurality of arcuate electrodes 100 being on the elongate body distal portion 62 and extending around less than an entirety of the circumference of the elongate body 54 such that each of the plurality of arcuate electrodes 100 defines a gap 101; and a reverse irrigation band 98 on the elongate body distal portion 62, the reverse irrigation band 98 being at least substantially parallel to the elongate body longitudinal axis 72 and extending within the gap 101 defined by each of the plurality of arcuate electrodes 100, the at least one reverse irrigation port 14 including a plurality of reverse irrigation ports 14 that are on the reverse irrigation band 98.

In one aspect of the embodiment, the reverse irrigation device 12 further comprises an elongate body 54 having a distal portion 62 including a distal end 64, and a proximal portion 56 opposite the distal portion 62, the at least one ablation electrode 28/92 including a distal tip electrode 92 coupled to the distal end 64 of the elongate body 54, the distal tip electrode 92 including a plurality of elongate portions 94, and the at least one reverse irrigation port 14 including a plurality of elongate reverse irrigation ports 14 alternating with the plurality of elongate portions 94 of the distal tip electrode 92.

In one aspect of the embodiment, each of the plurality of reverse irrigation ports 14 includes: a first portion defining an opening in the distal end of the elongate body; and a second portion 97 that is configured to channel fluid over the distal tip electrode and into the opening of the first portion of the at least one reverse irrigation port.

In one aspect of the embodiment, the fluid removal component is a vacuum pump 32.

In one embodiment, a reverse irrigation sheath 44 for use with a medical device comprises: at least one lumen 68 configured to be in fluid communication with a vacuum pump 32; and at least one reverse irrigation port 14 in fluid communication with the at least one lumen 68.

In one aspect of the embodiment, the at least one lumen 68 is a central lumen, the reverse irrigation sheath 44 further comprising: a wall, the wall at least partially defining the central lumen 68, the at least one reverse irrigation port 14 extending through the wall to the central lumen 68.

In one aspect of the embodiment, the at least one reverse irrigation port 14 includes a plurality of reverse irrigation ports 14, each of the plurality of reverse irrigation ports 14 having one of a linear shape and a circular shape.

In one aspect of the embodiment, the at least one reverse irrigation port 14 includes a mesh 108.

In one aspect of the embodiment, the reverse irrigation sheath 44 further comprises: a distal end 102 defining a distal opening 104, the distal opening 104 being in fluid communication with the at least one lumen 68.

In one aspect of the embodiment, the distal opening 104 has a scalloped shape.

In one embodiment, a medical system 10 comprises: a medical device 12, the medical device 12 including at least one ablation electrode 28/92 and at least one reverse irrigation port 14; an ablation system 16 in communication with the medical device 12; and a reverse irrigation system 18, the reverse irrigation system 18 including a vacuum pump 32, the vacuum pump 32 being in fluid communication with the at least one reverse irrigation port 14 such that the at least one reverse irrigation port 14 is configured to remove fluid from an ablation site during an ablation procedure.

In one aspect of the embodiment, the ablation system 16 includes processing circuitry 30 and an energy generator 26 in communication with the at least one ablation electrode 28/92; and the reverse irrigation system 18 includes processing circuitry 34 in communication with the vacuum pump 32 and the ablation system processing circuitry 30, the ablation system processing circuitry 30 and the reverse irrigation processing circuitry 34 being configured to operate synchronously such that the vacuum pump 32 is activated to remove fluid from the ablation site during a period of time during which the energy generator 26 is activated to deliver ablation energy through the at least one ablation electrode 28/92 to the ablation site.

In one embodiment, a medical system 10 comprises: a medical device 12, the medical device 12 including at least one ablation electrode 28/92 and at least one reverse irrigation port 14; an ablation system 16 in communication with the medical device 12; and a reverse irrigation system 18, the reverse irrigation system 18 being in communication with the ablation system 16 and being configured to: initiate a withdrawal of fluid from a treatment site through the at least one reverse irrigation port 14, the initiation being at a predetermined period of time before a delivery of ablation energy by the ablation system 16; and terminate the withdrawal of fluid a treatment site through the at least one reverse irrigation port 14, the termination being at a predetermined period of time after the delivery of ablation energy by the ablation system 16.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A reverse irrigation sheath for use with a medical device, the reverse irrigation sheath comprising:
    a proximal end and a distal end opposite the proximal end, the distal end defining a distal opening;
    at least one lumen configured to be in fluid communication with a vacuum pump and the distal opening, the at least one lumen being configured so that at least a portion of the medical device is extendable through the distal opening at the distal end;
    a first reverse irrigation port in fluid communication with the at least one lumen, the first reverse irrigation port being defined by the distal opening;
    a wall, the wall at least partially defining the at least one lumen; and
    a second plurality of reverse irrigation ports disposed in the wall and proximate to the distal end in an irregular patter, each reverse irrigation port from the second plurality of reverse irrigation ports having a dimeter; the diameters of the second plurality of reverse irrigation ports increasing in a proximal-to-distal direction between the proximal end and the distal end.

2. The reverse irrigation sheath of claim 1, wherein the at least one lumen is a central lumen.

3. The reverse irrigation sheath of claim 2, wherein each reverse irrigation port of the second plurality of reverse irrigation ports has a circular shape.

4. The reverse irrigation sheath of claim 1, wherein the diameter of each irrigation port in the second plurality of reverse irrigation ports increases in increments of 10 μm in a proximal-to-distal direction.

5. The reverse irrigation sheath of claim 1, wherein the diameter of each irrigation port in the second plurality of reverse irrigation ports increases in increments of 0.2 mm in a proximal-to-distal direction.

6. The reverse irrigation sheath of claim 1, wherein the number of reverse irrigation ports in the second plurality of reverse irrigation ports increases in a proximal-to-distal direction.

7. The reverse irrigation sheath of claim 1, wherein the reverse irrigation ports disposed farthest to the distal opening have the smallest diameter of the reverse irrigation ports in the second plurality of reverse irrigation ports.

8. The reverse irrigation sheath of claim 1, wherein the reverse irrigation ports disposed closest to the distal opening have the largest diameter of the reverse irrigation ports in the second plurality of reverse irrigation ports.

9. The reverse irrigation sheath of claim 1, wherein the first reverse irrigation port has a circular shape.

10. The reverse irrigation sheath of claim 1, wherein at least one reverse irrigation port from the second plurality of reverse irrigation ports has an elongate shape.

11. The reverse irrigation sheath of claim 10, wherein the elongate shape has a diameter that increases in size in a proximal-to-distal direction.

* * * * *